United States Patent
Yong et al.

(10) Patent No.: US 9,738,673 B1
(45) Date of Patent: Aug. 22, 2017

(54) FERROCENE DERIVATIVE, PREPARATION METHOD AND USE THEREOF

(71) Applicant: XIAMEN INSTITUTE OF RARE EARTH MATERIALS, Xiamen, Fujian (CN)

(72) Inventors: Jianping Yong, Fujian (CN); Canzhong Lu, Fujian (CN)

(73) Assignee: XIAMEN INSTITUTE OF RARE EARTH MATERIALS, Xiamen, Fujian (CN)

( * ) Notice: Subject to any disclaimer, the term of this patent is extended or adjusted under 35 U.S.C. 154(b) by 0 days.

(21) Appl. No.: 15/363,574

(22) Filed: Nov. 29, 2016

(30) Foreign Application Priority Data

Oct. 31, 2016 (CN) .......................... 2016 1 0930613

(51) Int. Cl.
C07F 17/02 (2006.01)
(52) U.S. Cl.
CPC .................................... C07F 17/02 (2013.01)
(58) Field of Classification Search
CPC ....................................................... C07F 17/02
See application file for complete search history.

(56) References Cited

FOREIGN PATENT DOCUMENTS

CN 103601762 A 2/2014

OTHER PUBLICATIONS

Sasada et al. "Immune Responses to Epidermal Growth Factor Receptor (EGFR) and Their Application for Cancer Treatment" Frontiers in Pharmacology, 2016, vol. 7, Article 405, pp. 1-7.*
Yong et al. "Synthesis of isoxazole moiety containing ferrocene derivatives and preliminarily in vitro anticancer activity" MedChemComm, 2014, vol. 5, pp. 968-972.*
Jianping Yong et al., "Synthesis of isoxazole moiety containing ferrocene derivatives and preliminarily in vitro anticancer activity", Med. Chem. Commun., 2014, vol. 5, p. 968-972.
Ahmedin Jemal et al., "Global Cancer Statistics", CA Cancer J. Clin. 2011, vol. (61), p. 69-90.
Ahmedin Jemal et al., "Cancer Statistics, 2010", CA Cancer J. Clin. 2010, vol. (60), p. 277-300.
Dharmendra Kumar Yadav et al., "Design, Synthesis and in Vitro Evaluation of 18β-Glycyrrhetinic Acid Derivatives for Anticancer Activity Against Human Breast Cancer Cell Line MCF-7", Current Medicinal Chemistry, 2014, vol. (21), p. 1160-1170.
Lei Fan et al., "Breast cancer in China", Lancet Oncol, vol. 15, Jun. 2014, p. 279-289.
Fuxing Xu, "Research Status of Colorectal", International Journal of Digestive Diseases, 2006, vol. 26, No. 6, p. 365-366.
De Lu Li et al., "Incidence and Mortality of Colorectal Cancer in Shanghai from 2003 to 2007", Chinese Journal of Cancer. 2011, 20 (6):413-418.

Eve I. Edwards et al., "Organometallic derivatives of penicillins and cephalosporins a new class of semi-synthetic antibiotics", Journal of Organometallic Chemistry. 1975, vol. 85, p. C23-C25.
Ayelet Rosenfeld et al., "Preparation, characterization and aitileukemic properties of diaminemalonatoplatinum(II) complexes tethered to ferrocene", Inorganica Chimica Acta, 1992, vol. 201, p. 219-221.
Elena I. Klimova et al., "Synthesis and biological evaluation of novel ethyl 2-amino-6-ferrocenyl-1,6-dihydropyrimidine-5-carboxylates and ethyl 2-amino-6-ferrocenylpyrimidine-5-carboxylates", Journal of Organometallic chemistry, 2012, vol. 708-709, p. 37-45.

(Continued)

*Primary Examiner* — Joseph Kosack
(74) *Attorney, Agent, or Firm* — Novick, Kim & Lee, PLLC; Allen Xue

(57) ABSTRACT

The present invention relates to the ferrocene derivative represented by formula (IA) or formula (IB), or to the pharmaceutically acceptable salt or solvate thereof and to the pharmaceutical composition thereof. Wherein, R is independently selected from H, halogen, cyano, nitro, $C_1$-$C_6$ alkyl, $C_1$-$C_6$ alkoxy, hydroxy-$C_1$-$C_6$ alkyl, halo-$C_1$-$C_6$ alkyl, halo-$C_1$-$C_6$ alkoxy or $C_1$-$C_6$ alkoxy-$C_1$-$C_6$ alkoxy; Z is selected from O, S or $NR_1$, wherein $R_1$ is independently H or $C_1$-$C_6$ alkyl; n is an integer from 0 to 5. The present invention also provides a method and the pharmaceutical application thereof for preparing the compounds represented by formula (IA) or formula (IB) or the pharmaceutically acceptable salts thereof. The compounds have a strong inhibitory activity against human lung cancer cell line A549, colorectal cancer cell line HCT116 and/or breast cancer cell line MCF-7.

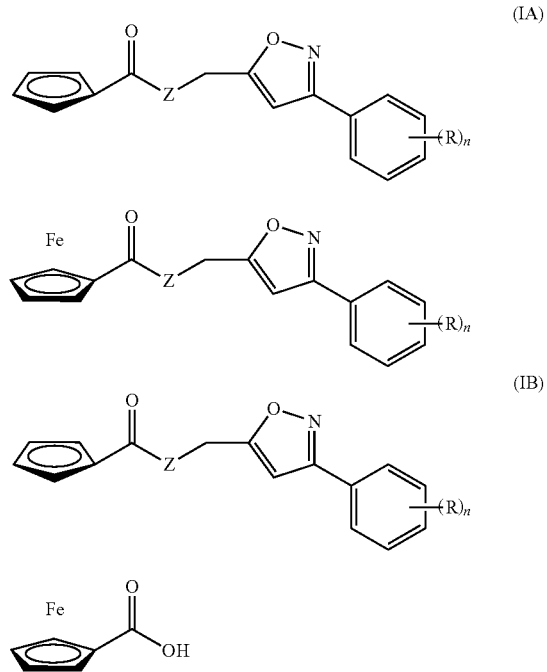

17 Claims, No Drawings

(56) References Cited

OTHER PUBLICATIONS

Xian-Feng Huang et al., "Synthesis, characterization and antitumor activity of novel amide derivatives containing ferrocenyl pyrazol-moiety", Journal of Organometallic Chemistry, 2012, vol. 706-707, p. 113-123.
Wei Liu et al., "Synthesis, characterization and bioactivity determination of ferrocenyl urea derivatives".
Eberhard W. Neuse, "Macromolecular Ferrocene Compounds as Cancer Drug Models", Journal of Inorganic and Organometallic Polymers and Materials, vol. 15, No. 1, Mar. 2005.
Susana S. Braga et al., "A New Age for Iron: Antitumoral Ferrocenes", Organometallics, 2013, vol. 32, p. 5626-5639.
Jun She et al., "Lung Cancer in China Challenges and Interventions", Chest. 2013, vol. 143(4), p. 1117-1126.

* cited by examiner

FERROCENE DERIVATIVE, PREPARATION METHOD AND USE THEREOF

TECHNICAL FIELD

The present invention belongs to the field of pharmaceutical chemistry, and relates to novel ferrocene derivatives of the type A and B; particularly, relates to a method for preparing of the ferrocene derivatives and the pharmaceutical compositions containing same and use thereof.

The ferrocene derivatives have strong inhibitory activity against human lung cancer cell line A549, colorectal cancer cell line HCT116 and breast cancer cell line MCF-7. The compounds have wide anticancer activity and can be used as candidate compounds or lead compounds for the treatment of diseases such as tumors or cancers, etc.

BACKGROUND OF THE INVENTION

Cancer has become the worldwide deadliest disease, and the proportion of deaths from cancers is very high in developed countries. Cancer can occur in a variety of organs and tissues at any age, and the main types of cancer leading to the death are: lung cancer, stomach cancer, liver cancer, colon cancer, breast cancer, and so on. In recent years, lung cancer has become the highest incidence rate of malignant tumors. According to World Health Organization (WHO) statistics, 1,600,000 people were diagnosed with lung cancer all over the word in 2008, accounting for 13% of the total cancer incidence, and 1,400,000 deaths, accounting for 18% of all cancer deaths (Jemal A, et al. C A Cancer J. Clin. 2011, 61: 69-90); in 2010, a total of 222,520 new lung cancer cases and 157,330 cancer deaths occurred in the United States, who died from non-small cell lung cancer (NSCLC), accounting for 85% of all cases of lung cancer (Jemal A, et al. C A Cancer J. Clin. 2010, 60: 277-300). In recent years, among the top 10 malignant tumors in China's urban and rural areas, lung cancer has replaced liver cancer and ranked as the first leading cause of mortality among people with malignant tumors in China, accounting for 22.7% of all malignant tumor deaths (She J, et al. Chest. 2013, 143(4): 1117-1126). Breast cancer is the most common cancer among women worldwide currently facing, with about 1,380,000 new cases of breast cancer diagnosed and 458,000 deaths each year. According to reports, 232,340 new cases of breast cancer in the United States were diagnosed each year. In 2011, in the United States, nearly 40,000 women died from breast cancer; in India, 100,000 new cases of breast cancer were diagnosed each year, and one in 28 women developed to breast cancer (Yadav D K, et al. Curr. Med. Chem. 2014, 21(9): 1160-1170); in China, breast cancer has also become the most common cancer among women, with a total of 169,452 new cases of breast cancer diagnosed and 449,08 cases deaths until 2008, accounting for 12.2% and 9.6% of the world total, respectively. The total number of breast cancer cases diagnosed in China was half of those in Europe (332,000 cases in the overall population of 498 million in 2008), and roughly the same as in the United States (182,000 cases in the overall population of 304 million in 2008). If the trend remains constant, in China, breast cancer patients will be as high as 2,500,000 by 2021, with incidence rates increasing from less than 60 cases per 100,000 females (between the age of 55 and 69) to more than 100 cases per 100,000 females (Fan L, et al. Lancet Oncol. 2014, 15: e279-289). Globally, the number of women suffering from breast cancer is increasing, which poses a great threat to the survival of women. Colon cancer and rectal cancer are collectively called the colorectal cancer, which is a common malignant tumor of digestive tract, with incidence rates increasing an average of 2% per year, ranking second in cancer mortality in Europe and the United States, and ranking third in both incidence and mortality from cancer in the United State in 2003 (Xu, Fu Xing. International Journal of Digestive Diseases 2006, 26 (6): 365-366). In recent years, the incidence of colorectal cancer in China has risen dramatically, on a national scale, to the fourth in malignant tumor, and has ranked second in some fast-growing cities such as Shanghai (Li, De Lu, et al. Chinese Journal of Cancer. 2011, 20 (6): 413-418).

However, because most cancers are found in their medium or late stages, overall effects of clinical treatment are poor, and especially multidrug resistance continues to emerge, which makes the treatment of cancer difficult. Therefore, we must develop new anticancer drugs with high activities and low side effects to meet clinical needs.

Ferrocene, synthesized by Kealy and Pauson in 1951, has a unique sandwich structure with the divalent iron ions located between two plane rings being in a staggered conformation. Along with constantly deepening of research, various structure of ferrocene derivatives have been synthesized at home and abroad. Particularly in the field of pharmaceutical chemistry, the ferrocene derivatives show more pronounced activities: E. I. Edwards, et al. introduced ferrocenyl moieties into penicillin and cephalosporin, resulting in greatly improving the bactericidal activity (E I Edwards, et al. J. Organomet. Chem. 1975, 85: $C_{23}$); the research done by A. R. Tajcrak, et al. showed that the ferrocene derivatives have insecticidal activity; the research done by A. Rosenefeld, et al. showed that the ferrocene-modified cisplatin derivatives have very strong inhibitory activity against leukemia, and the nephrotoxic is much lower than cis-DDP (A. Rosenfeld, et al. Inorg. Chim. Acta. 1992, 201:219); the research done by E. I. Klimova, et al. showed that the cyclopropane-containing ferrocene derivatives have strong anti-inflammatory activity (E. I. Klimova, et al. J. Organomet. Chem. 2012, 708-709: 37-45); X. F. Huang et al. synthesized a series of ferrocene derivatives containing pyrazole rings, and the activity studies showed that some of the compounds have stronger anticancer activities than 5-fluorouracil (X. F. Huang, et al. J. Organomet. Chem. 2012, 706-707: 113-123); W. Liu et al. synthesized a series of ferrocene derivatives containing urea, and the activity studies showed that some compounds have strong inhibition activity against HIV-1 protease (W. Liu, et al. Appl. Organomet. Chem. 2012, 26: 189-193); ferrocene-quinoline derivatives

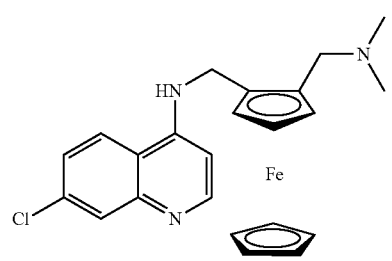

(FQ, SSR97193) have strong antimalarial activity, and have entered phase II clinical research.

U.S. patent application No. 8426462B2 disclosed that the ferrocene derivatives containing aromatic rings have strong inhibitory activity against human breast cancer cell line MDA-MB-231 and prostate cancer cell line PC-3.

In recent years, our research team has been devoted to the study of the design, synthesis and anticancer activity studies of small-molecule anticancer drugs. Ferrocene is a lead compound for the design and synthesis of antitumor drugs (E. W. Neuse. J. Inorg. Organomet. P. 2005, 15(1):3-32; S. S. Braga, et al. Organometallics, 2013, 32: 5626-5639). In our previous work, we designed and synthesized a series of novel structure ferrocene-carboxylic acid derivatives, studied their initial anticancer activities, and the results showed that most of the compounds have stronger anticancer activity than the positive controlling drug Gefitinib (Yong, Jianping, et al. Application Publication No. CN103601762A). Based on the good results achieved in our patent application publication No. CN103601762A, we continue to design and synthesize ferrocene derivatives with novel structures to find lead compounds or candidate compounds for clinical use.

DETAILED DESCRIPTION OF THE INVENTION

The object of the present invention is to provide novel structure ferrocene derivative represented by formula (IA) or formula (TB). The research results of in-vitro inhibitory activity against colorectal cancer cell line HCT116, human lung cancer cell line A549, and/or breast cancer cell line MCF-7 show that the compounds have strong inhibitory activity against colorectal cancer cell line HCT116, human lung cancer cell line A549, and/or breast cancer cell line MCF-7, and can be used as candidate compounds or lead compounds for anticancer drugs.

The invention is realized by the following technical solutions:

A ferrocene derivative represented by formula (IA) or formula (TB), or the pharmaceutically acceptable salt or solvate thereof,

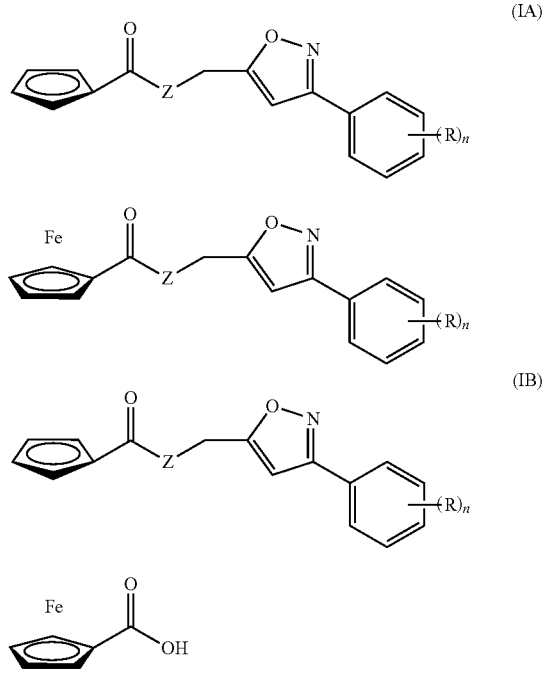

wherein:
Z is selected from O, S or $NR_1$, wherein $R_1$ is independently H or $C_1$-$C_6$ alkyl; R is independently selected from H, halogen, cyano, nitro, $C_1$-$C_6$ alkyl, $C_1$-$C_6$ alkoxy, hydroxy-$C_1$-$C_6$ alkyl, halo-$C_1$-$C_6$ alkyl, halo-$C_1$-$C_6$ alkoxy or $C_1$-$C_6$ alkoxy-$C_1$-$C_6$ alkyl;

n is an integer from 0 to 5, when n is more than 1, the R group may be the same or different.

According to the preferred technical solution of the present invention, in formula (IA) or formula (TB):

Z is selected from O or $NR_1$, wherein $R_1$ is independently H or $C_1$-$C_4$ alkyl;

R is independently selected from H, halogen, cyano, nitro, $C_1$-$C_4$ alkyl, $C_1$-$C_4$ alkoxy, hydroxy-$C_1$-$C_3$ alkyl, halo-$C_1$-$C_4$ alkyl;

n is an integer from 0 to 5.

According to the more preferred technical solution of the present invention, in formula (IA) or formula (IB):

Z is selected from 0 or NH;

R is independently selected from hydrogen, fluoro, chloro, bromo, methyl, ethyl, t-butyl, methoxy, nitro, cyano or trifluoromethyl;

n is an integer of 0, 1, 2, or 3.

According to the present invention, said ferrocene derivative represented by formula (IA) or formula (TB) is selected from any of the following compounds:

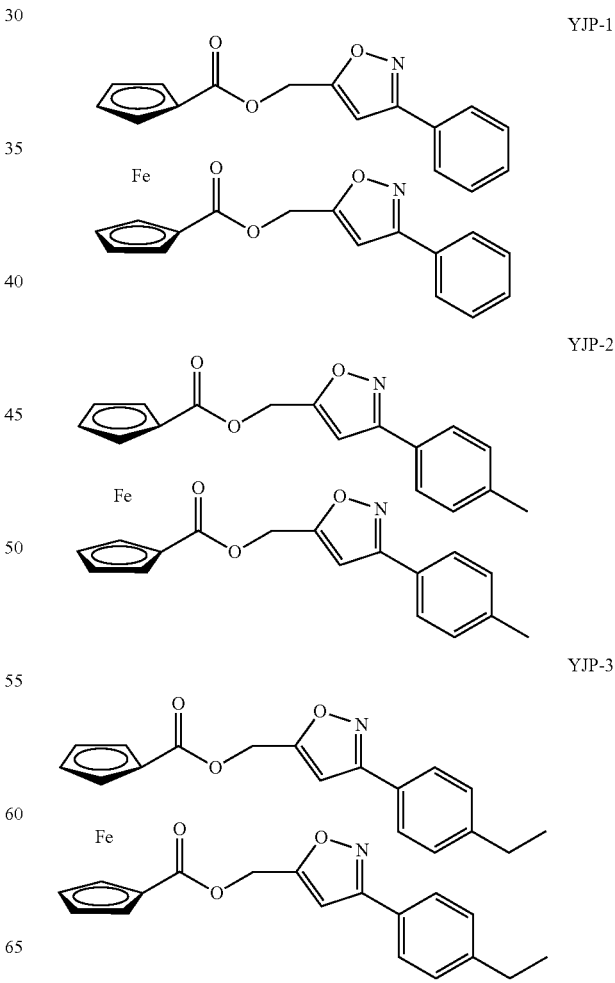

-continued
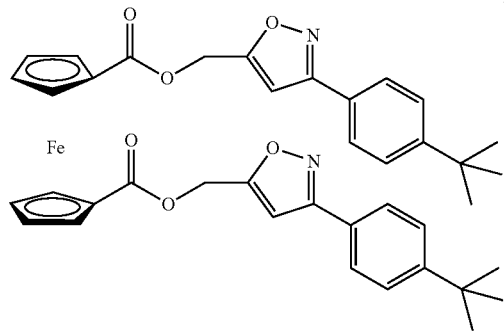
YJP-4
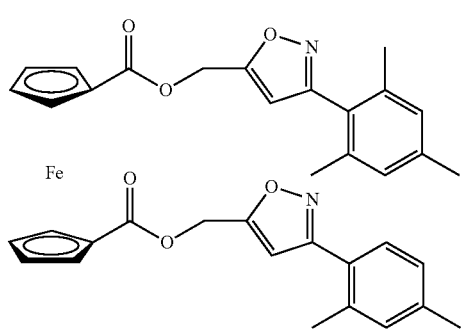
YJP-5
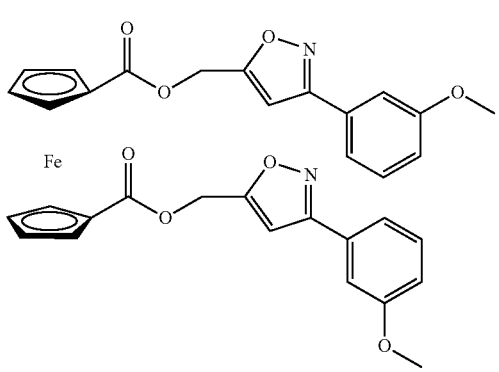
YJP-8
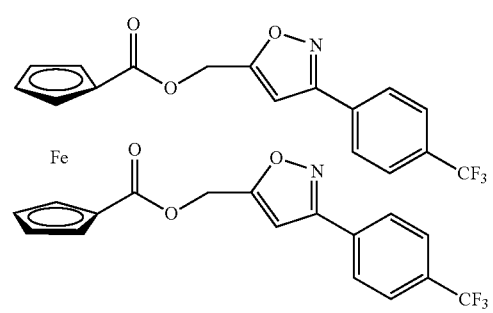
YJP-9
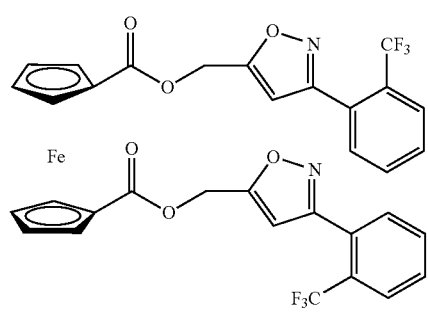
YJP-10
-continued
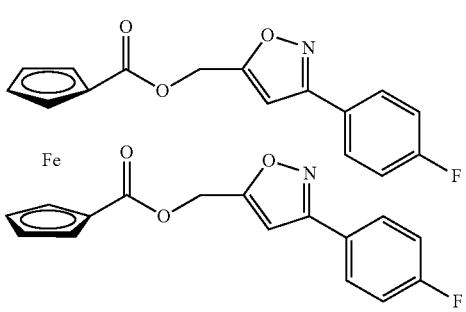
YJP-6
YJP-7
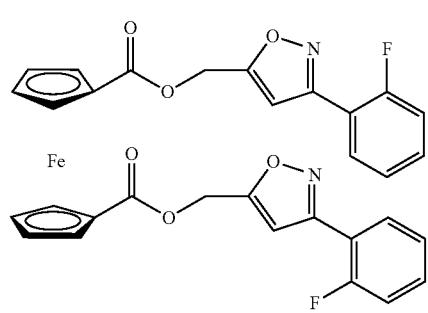
YJP-11
YJP-12

YJP-13
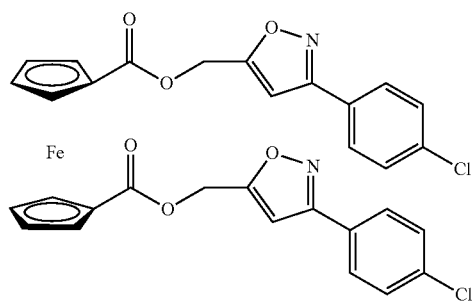
YJP-14
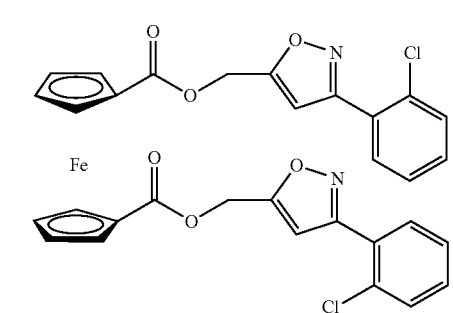
YJP-15
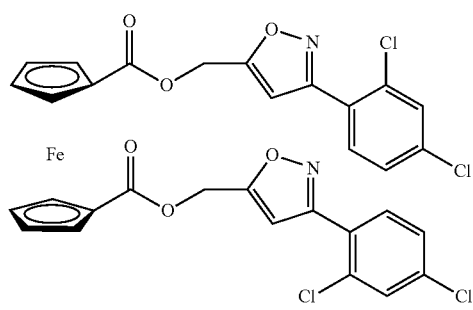
YJP-16
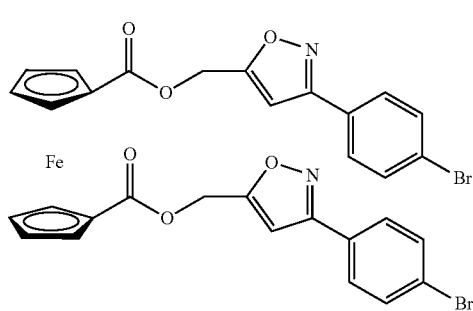
YJP-17
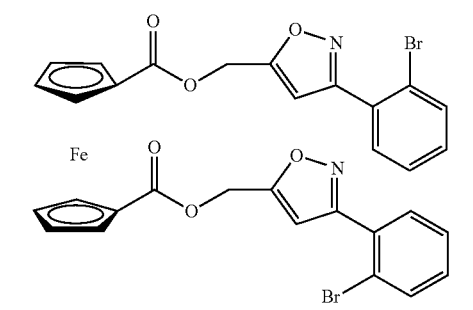
YJP-18
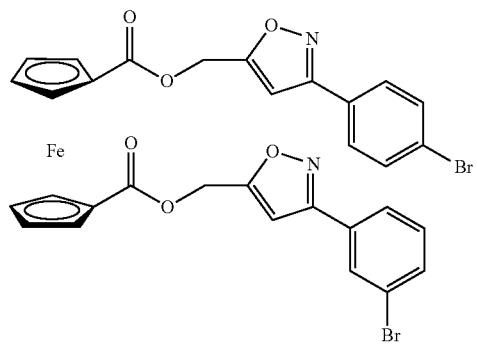
YJP-19
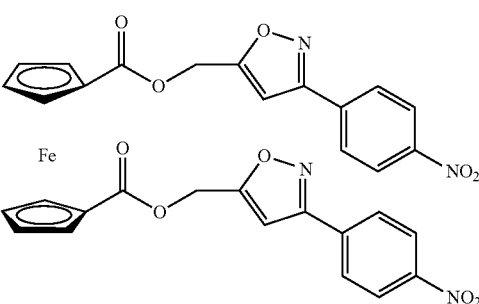
YJP-20
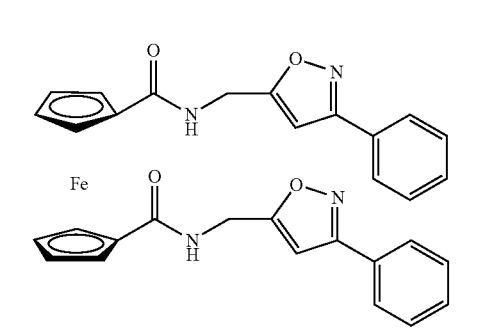
YJP-21
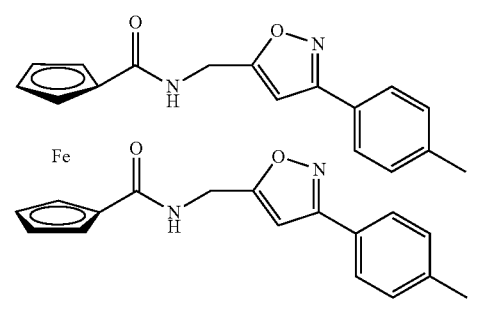
YJP-22
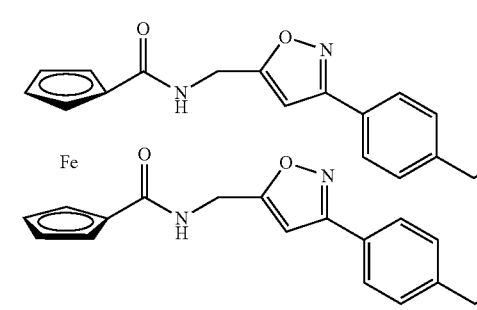

YJP-23
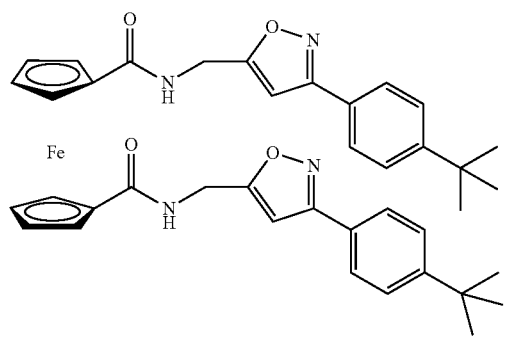
YJP-24
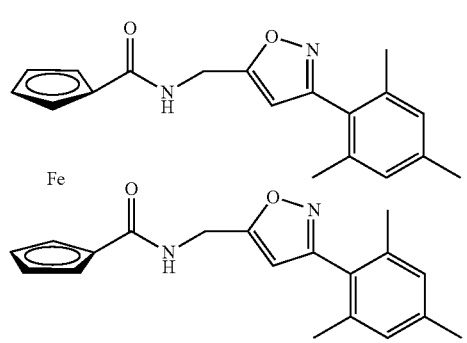
YJP-25
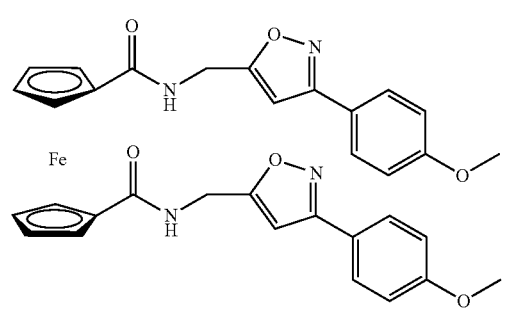
YJP-26
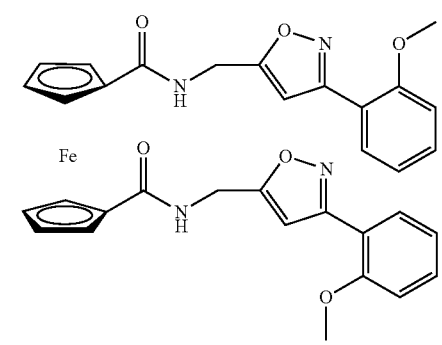
YJP-27
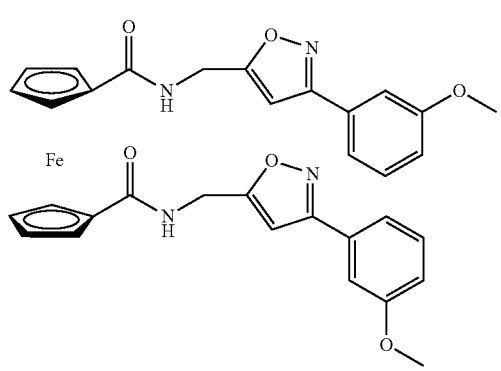
YJP-28
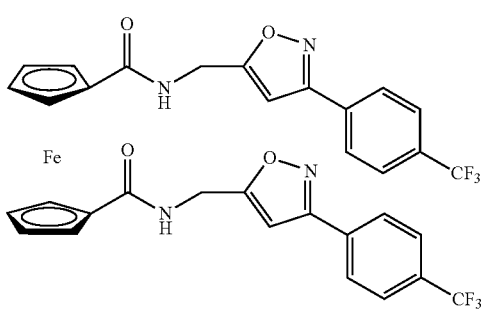
YJP-29
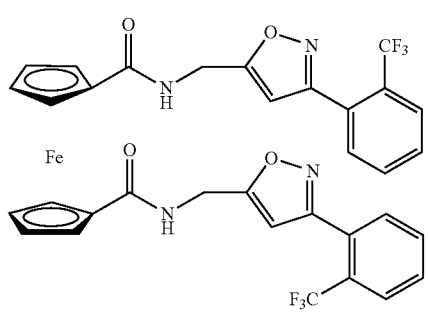
YJP-30
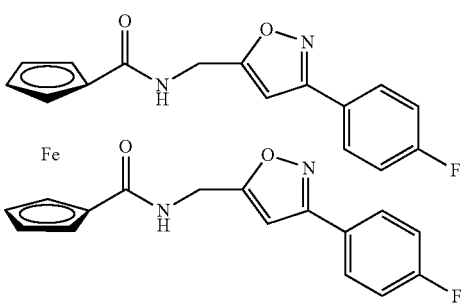
YJP-31
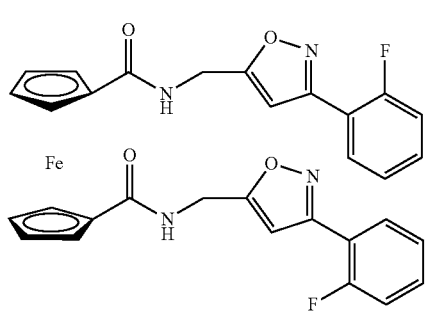

YJP-32
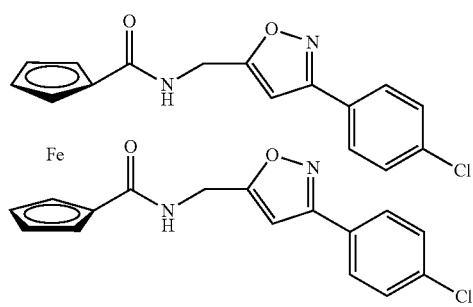
YJP-33
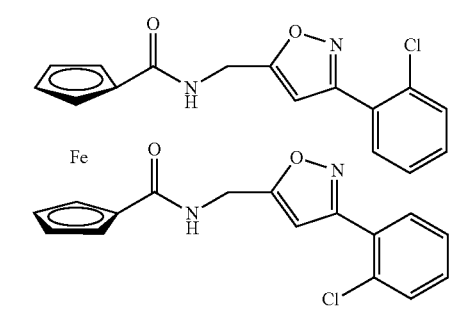
YJP-34
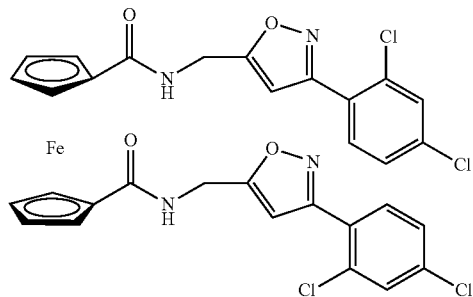
YJP-35
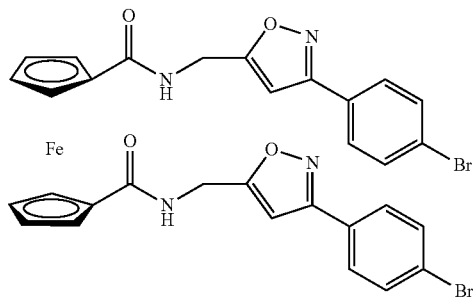
YJP-36
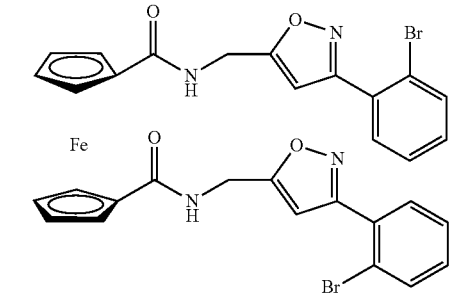
YJP-37
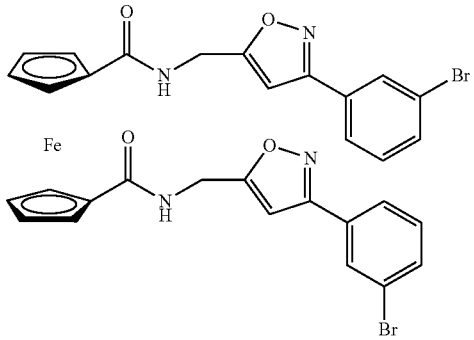
YJP-38
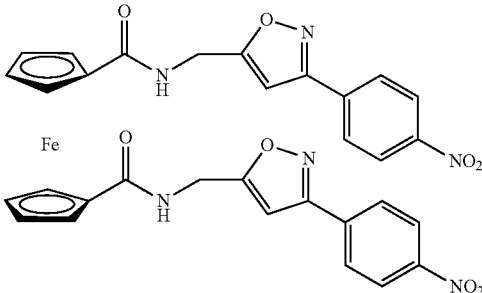
YJP-39
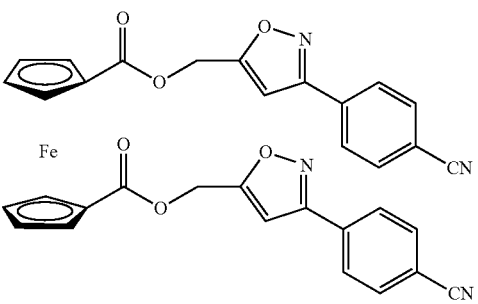
YJP-40
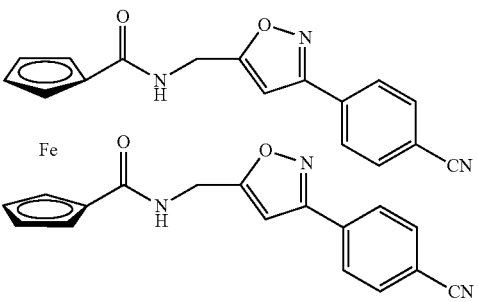
YJP-41
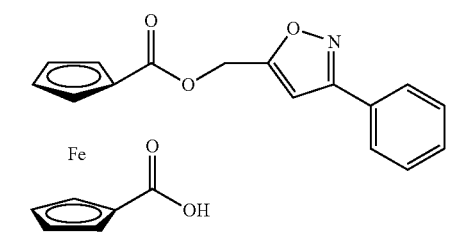

YJP-42

YJP-43

YJP-44

YJP-45

YJP-46

YJP-47

YJP-48

YJP-49

YJP-50

YJP-51

YJP-52

YJP-53

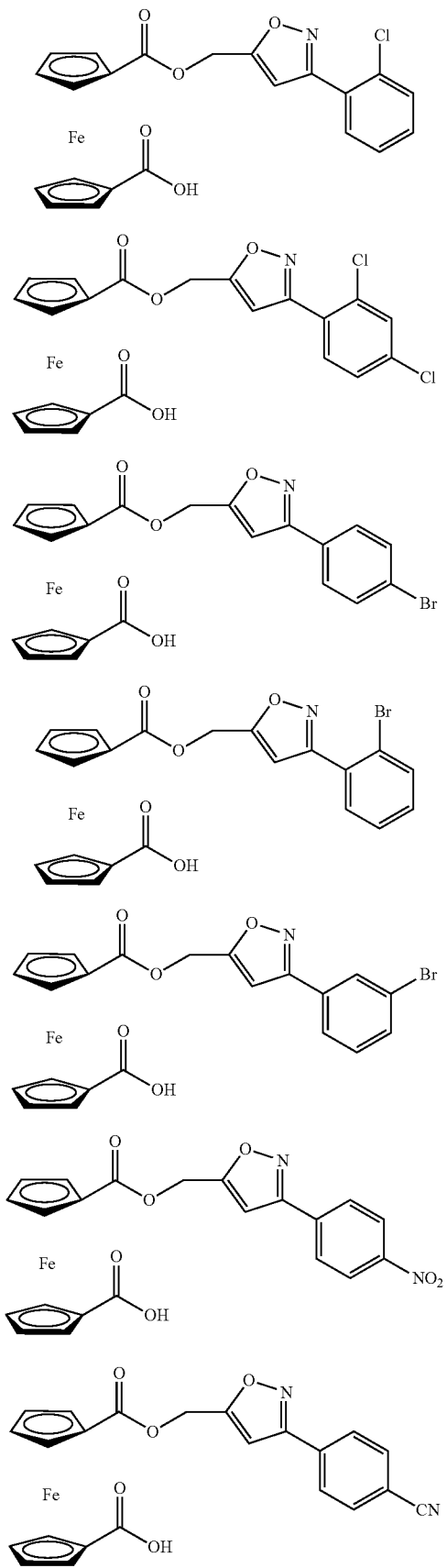
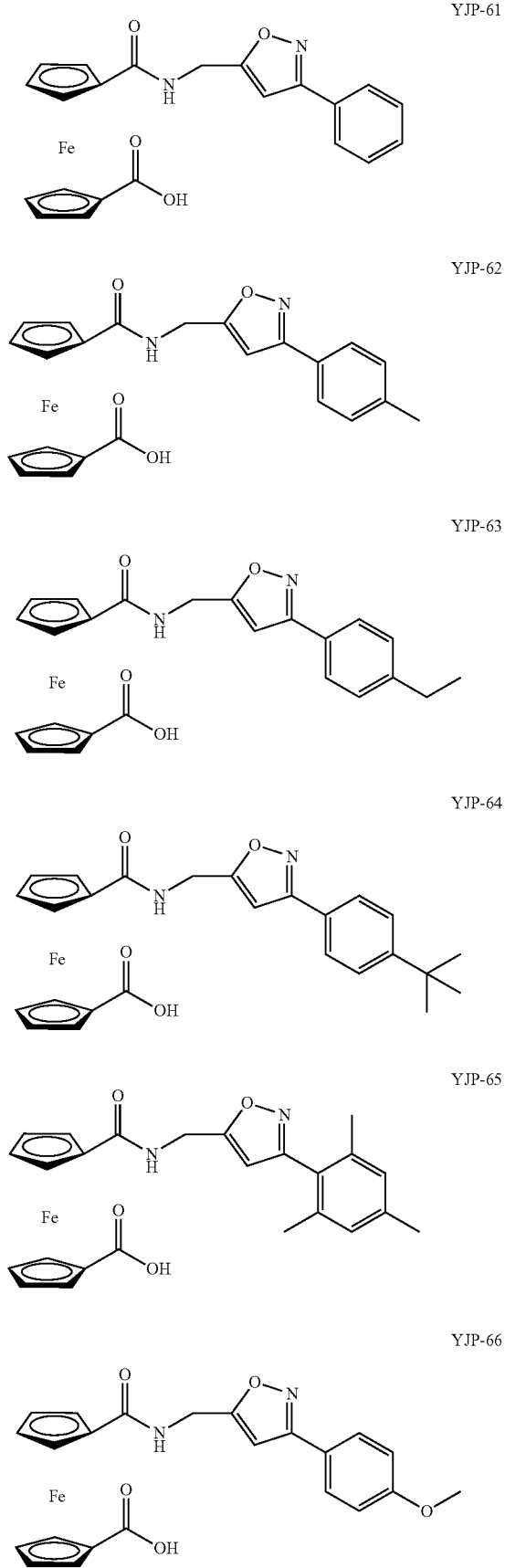

YJP-67
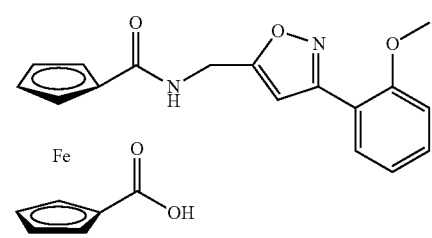
YJP-68
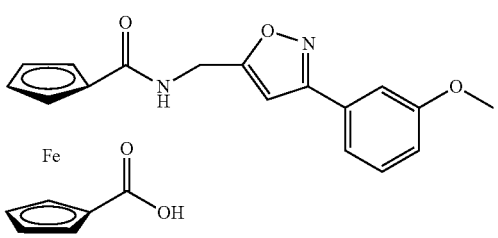
YJP-69
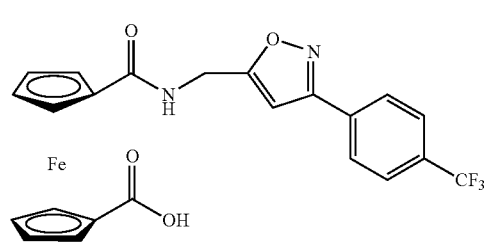
YJP-70
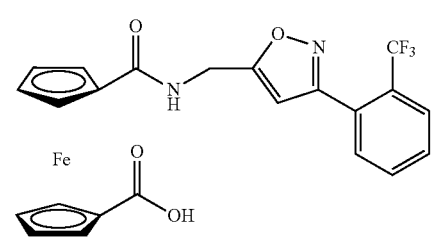
YJP-71
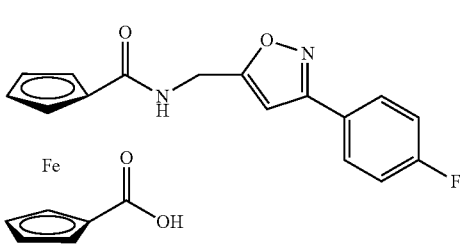
YJP-72
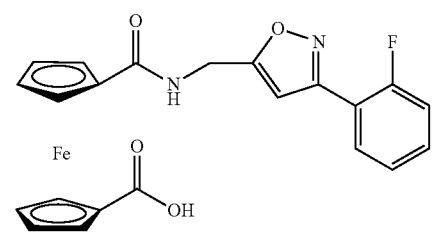
YJP-73
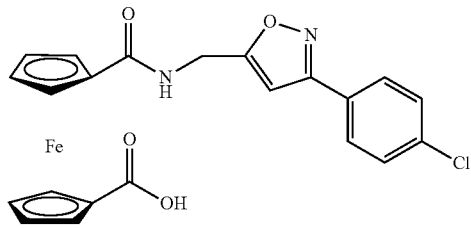
YJP-74
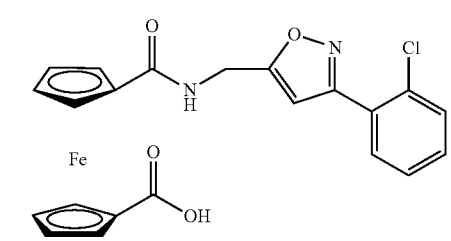
YJP-75
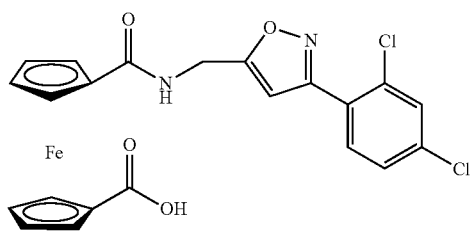
YJP-76
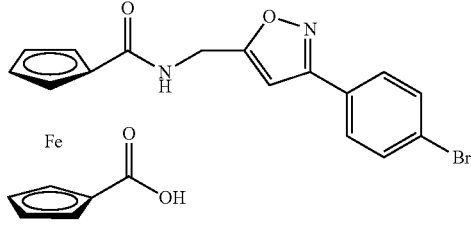
YJP-77
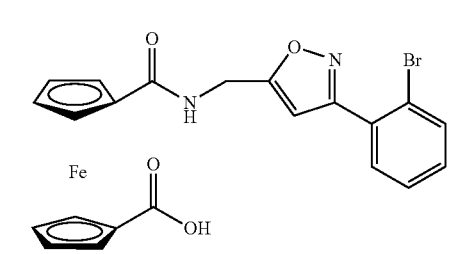
YJP-78
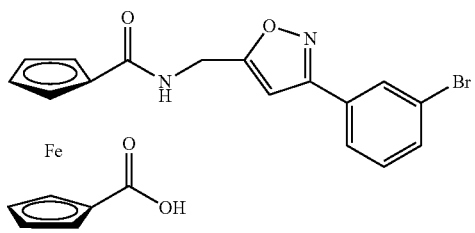

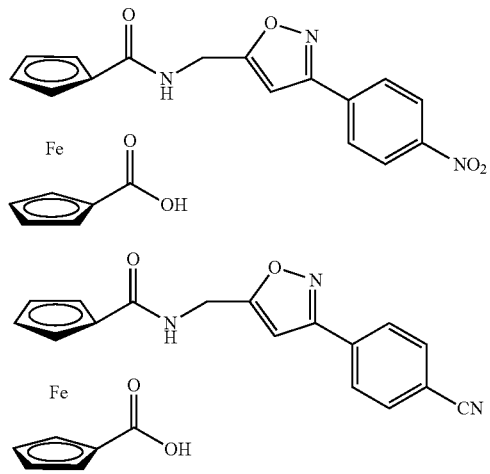

YJP-79

YJP-80

In the present invention, the ferrocene derivative represented by formula (IA) or (IB) may be respectively selected to form a pharmaceutically acceptable salt with a pharmaceutically acceptable acid. Wherein, the term "pharmaceutically acceptable salt" includes, but is not limited to a salt formed with an inorganic acid, such as hydrochloride, phosphate, diphosphate, hydrobromide, sulfate, sulfinate, nitrate, and similar salts thereof; and also includes a salt formed with an organic acid, such as lactate, oxalate, malate, maleate, fumarate, tartrate, succinate, citrate, sulfonate, p-toluene sulfonate, 2-hydroxyethyl sulfonate, benzoate, salicylate, stearate, trifluoroacetate, amino acid salt, or alkanoate such as acetate, HOOC—$(CH_2)_m$—COOH salt (wherein, the m is an integer from 1 to 4), and similar salts thereof. Similarly, a pharmaceutically acceptable cation includes, but is not limited to sodium, potassium, calcium, aluminum, lithium and ammonium.

The term "solvate" includes a hydrate and an alcoholate.

The present invention also provides a pharmaceutical composition comprising the ferrocene derivative represented by formula (IA) or (IB), or the pharmaceutically acceptable salt or solvate thereof, and comprising at least one pharmaceutically acceptable, inert, non-toxic excipient, carrier or diluent.

According to said pharmaceutical composition, wherein, said pharmaceutical composition also comprises one or more pharmaceutically acceptable auxiliaries selected from a filler, a disintegrating agent, a lubricant, a glidant, an effervescent agent, a flavoring agent, a preservative and a coating material.

The present invention also provides a pharmaceutical preparation comprising the ferrocene derivative represented by formula (IA) or (IB), or the pharmaceutically acceptable salt or solvate thereof, and comprising at least one pharmaceutically acceptable, inert, non-toxic excipient, carrier or diluent.

The present invention provides a pharmaceutical preparation, wherein, said pharmaceutical preparation is preferably a solid oral preparation, a liquid oral preparation or an injection.

According to the pharmaceutical preparation of the present invention, said preparation is selected from a tablet, a dispersible tablet, an enteric coated tablet, a chewable tablet, an orally disintegrating tablet, a capsule, a granule, an oral soluble formulation, water for injection, a lyophilized powder for injection, large volume infusion or small volume infusion.

The present invention also provides any of the above-mentioned of the ferrocene derivative represented by formula (IA) or (IB), or the pharmaceutically acceptable salt or solvate thereof for medicament, which is particularly utilized in the preparation of antitumor drugs for the effective treatment of inhibiting the overexpression and/or overactivity of EGFR.

The present invention also provides any of the above-mentioned of the ferrocene derivative represented by formula (IA) or (IB), or the pharmaceutically acceptable salt or solvate thereof, which is used in the preparation of antitumor or anticancer drugs.

According to said application of the present invention, wherein, said tumor or cancer is selected from: bladder cancer, non-small cell lung cancer, ovarian cancer, breast cancer, stomach cancer, esophageal cancer, lung cancer, head and neck cancer, colon cancer, pharyngeal cancer and pancreatic cancer, and so on, more preferably is non-small cell lung cancer.

The present invention also provides any of the above-mentioned of the ferrocene derivative represented by formula (IA) or (IB), or the pharmaceutically acceptable salt or solvate thereof, which is used in the preparation of an inhibitor for inhibiting the overexpression and/or overactivity of EGFR.

The present invention also provides a method for preparing the ferrocene derivative represented by formula (IA) or (IB), wherein, said method includes the following steps:

A) carrying out a condensation reaction between a compound of formula (III) and a compound of formula (II) in a system of an organic solvent (preferably a dry organic solvent) and an alkaline acid binding reagent to obtain the compound of formula (IA):

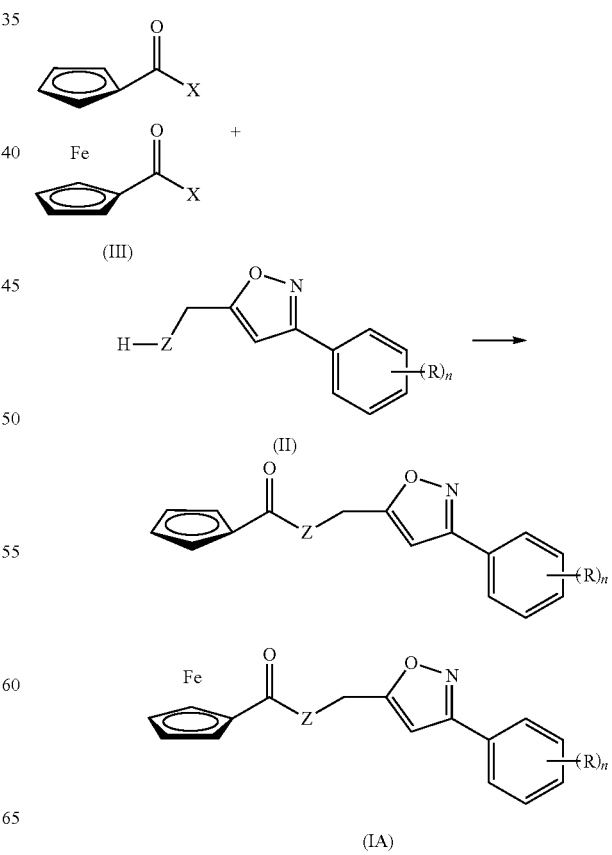

wherein, X is optionally OH or Cl; Z, R and n are as defined above;

or,

B) carrying out a condensation reaction between 1,1'-ferrocenedicarboxylic acid and a compound of formula (II) in a system of an organic solvent (preferably a dry organic solvent) and an alkaline catalyst to obtain the compound of formula (IB):

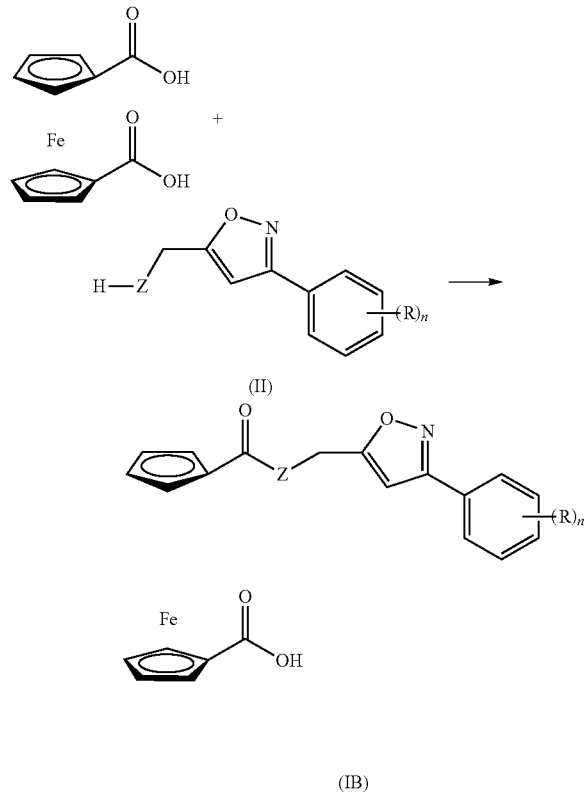

wherein, Z, R and n are as defined above;
any functional group in the compound of formula (II), if desired, can be protected.

And thereafter, if necessary (in any order):
(1) removing any protective reagent, and
(2) forming a pharmaceutically acceptable salt or solvate of the compound of formula (IA) or formula (IB).

According to the present invention, said reaction temperature is from −20° C. up to reflux conditions, preferably from 0° C. to room temperature.

According to the present invention, said reaction is carried out in an organic solvent, preferably a dry organic solvent. Said organic solvent can be benzene, toluene, xylene, dichloromethane, chloroform, acetonitrile, dioxane, tetrahydrofuran or DMF, more preferably tetrahydrofuran.

According to the present invention, said alkaline catalyst is an organic base or an inorganic base, said organic base is preferably selected from triethylamine, tripropylamine, DMAP, potassium tert-butoxide, and so on; said inorganic base is preferably selected from potassium carbonate, sodium hydride, sodium carbonate, and so on. Said alkaline acid binding reagent can also be the above-mentioned alkaline catalyst, the preferred acid binding reagent is DMAP. In the above-described condensation reaction, a condensation reagent, such as DCC, HOBt (1-hydroxybenzotriazole), and so on, can also be added.

According to the present invention, a compound of formula (II), when Z is O, can be prepared by the following method:

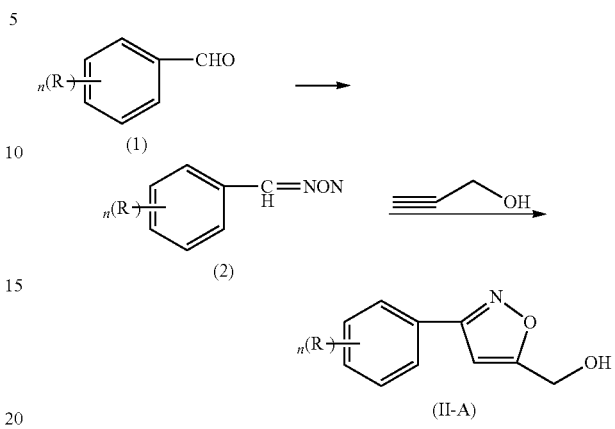

wherein, R and n are as defined above;
converting substituted benzaldehyde (a compound of formula (1)) to substituted benzaldoxime (a compound of formula (2)) (such as adding NH$_3$OH.HCl and sodium carbonate, reacting at 25° C.), and converting substituted benzaldoxime (a compound of formula (2)) to the compound of formula (II-A) via 1,3-dipolar cycloaddition reaction (such as adding propynol, NCS and Et$_3$N, refluxing at 0° C.).

A compound of formula (II), when Z is S, can be prepared by the following method:

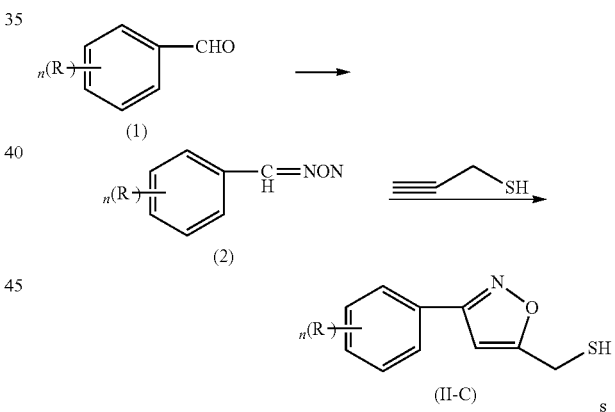

wherein, R and n are as defined above;
converting substituted benzaldehyde (a compound of formula (1)) to substituted benzaldoxime (a compound of formula (2)), and converting substituted benzaldoxime (a compound of formula (2)) to the compound of formula (II-C) via 1,3-dipolar cycloaddition reaction (propargylmercaptan).

A compound of formula (II), when Z is NH, can be prepared by the following method:

1) converting a compound of formula (II-A) via methylsulfonyl-esterification reaction (such as adding MSCl and Et$_3$N, reacting at 0° C.), azidation (such as adding NaN$_3$, reacting at 60° C.), and reduction (such as adding Zn and NH$_4$Cl, refluxing) to the compound of formula (II-B):

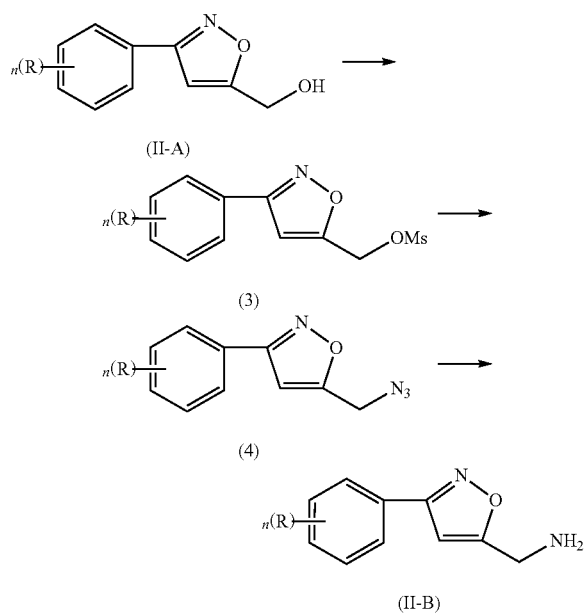

wherein, R and n are as defined above;

or 2) reacting substituted benzaldoxime (a compound of formula (2)) and propargylamine via 1,3-dipolar cycloaddition reaction (such as adding NCS and Et₃N, refluxing at 0° C.) to obtain the compound of formula (II-B);

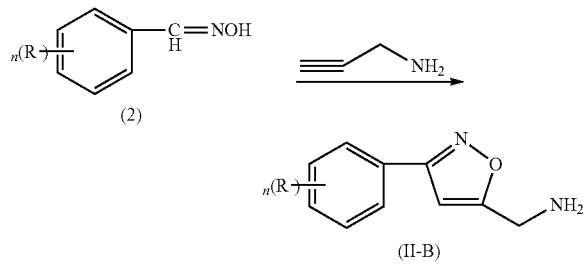

wherein, R and n are as defined above;

or 3) reacting substituted benzaldoxime (a compound of formula (2)) and 3-halo-propynyl via 1,3-dipolar cycloaddition reaction (such as adding NCS and Et₃N, refluxing at 0° C.) to obtain the compound of formula (5), followed by amine substitution reaction (such as adding ammonia) to obtain the compound of formula (II-B);

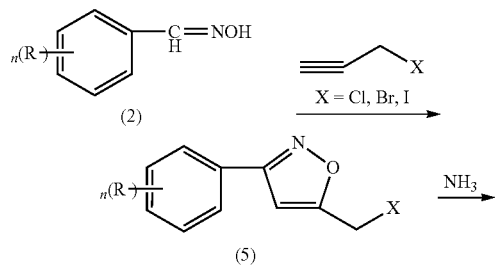

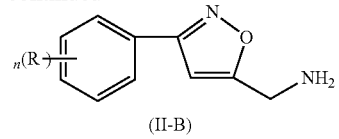

wherein, R and n are as defined above.

A compound of formula (II), when Z is $NR_1$, $R_1$ is $C_1$-$C_6$ alkyl, can be prepared by substitution reaction of a compound of formula (II-B) with an amino group.

The ferrocene derivative represented by formula (IA) or formula (IB) of the present invention include, but is not limited to their optical isomers, racemates and the mixtures.

The term "an effective amount" refers to the amount of at least one compound and/or at least one pharmaceutically acceptable salt that is effective for the "treatment" of an individual's disease or discomfort. If it is a cancer, the effective amount may reduce the number of cancer or tumor cells; shrink the size of the tumor; inhibit or prevent the tumor cell infiltration into peripheral organs, for example, when tumors spread into soft tissue or bone; inhibit or prevent tumor metastasis; inhibit or prevent tumor growth; to certain extent, relieve one or more symptoms associated with the cancer; reduce morbidity and mortality; improve quality of life; or a combination of the above-mentioned effects. The effective amount can be an amount which decreases the symptoms of a disease via inhibiting EGFR activity. For the treatment of cancer, the effect of in-vivo experiment can be measured by assessing, such as the duration of survival, time to disease progression (TTP), response rates (RR), the duration of sustained response and/or quality of life.

The effective amount may vary, as recognized by those professionals, along with a route of administration, a dosage of excipient, and co-usage with other drugs.

The term "an effective amount" may also refer to the dosage of at least one said compound and/or at least one pharmaceutically acceptable salt that is effective to inhibit the overexpression and/or overactivity of EGFR.

The ferrocene derivative of the present invention have an antitumor and anticancer activity, especially to human lung cancer cell line A549, colorectal cancer cell line HCT116 and/or breast cancer cell line MCF-7 with a strong inhibitory activity. $IC_{50}$ of the compound YJP-8 against the three tumor cell lines, A549, HCT116 and MCF-7, are 142.4 µM, 236.0 µM, 137.8 µM, respectively; $IC_{50}$ of the compound YJP-12 against the three tumor cell lines, A549, HCT116 and MCF-7, are 167.5 □M, 148.9 µM, 158.8 µM, respectively; $IC_{50}$ of the compound YJP-13 against the three tumor cell lines, A549, HCT116 and MCF-7, are 690.3 µM, 486.2 µM, 169.1 µM, respectively; $IC_{50}$ of the compound YJP-14 against the three tumor cell lines, A549, HCT116 and MCF-7, are 450.0 µM, 227.6 µM, 171.7 µM, respectively; $IC_{50}$ of the compound YJP-15 against the three tumor cell lines, A549, HCT116 and MCF-7, are 222.4 µM, 233.5 µM, 189.8 µM, respectively; $IC_{50}$ of the compound YJP-16 against the three tumor cell lines, A549, HCT116 and MCF-7, are 250.7 µM, 63.9 µM, 155.8 µM, respectively; $IC_{50}$ of the compound YJP-19 against the three tumor cell lines, A549, HCT116 and MCF-7, are 530.5 µM, 157.0 µM, 178.0 µM, respectively.

Most of the compounds are shown to have a strong inhibitory activity against the three tumor cell lines. The ferrocene derivative of the present invention can be used as candidate compounds or lead compounds for the treatment of tumors and cancers.

DETAILED DESCRIPTION OF VARIOUS EXAMPLES

In the following, the present invention will be further illustrated by means of specific examples. It should be understood that the examples are only intended to illustrate the invention, rather than to constitute a limitation of the scope of the present invention. In addition, it should be understood that such various changes or modifications as may be made by those skilled in the art after reading the description of the present invention would be considered to be equivalent fall equally within the scope of the present invention.

Among them, the synthetic processes of intermediates and target compounds are represented by the examples in EXAMPLES, and the synthetic processes of the other intermediates and target compounds are the same as those of the representative compounds.

Instruments and reagents: AVANCE III NMR (400 MHz, DMSO-$d_6$, TMS as an internal standard), ion trap liquid-mass spectrometer (DECAX-30000 LCQ Deca XP), XT5 micro melting point detector with digital display (Beijing Tech-Instrument Lighting Manufacturing, temperature without correction), wavelength-tunable microplate reader (Molecular Devise SPECTRAMAX190). Chemical reagents are commercially analytical reagents or chemically pure reagents, RPMI1640 (Gibco), MTT [3-(4,5-dimethylthiazol-2-yl)-2,5-diphenyltetrazolium bromide] (Sigma), other reagents are commercially analytical reagents and untreated before use unless otherwise specified, and tetrahydrofuran is treated with dry molecular sieves before use.

Example 1 The Synthesis of the Intermediate of 3-substituted phenyl-5-hydroxymethyl-isoxazole of Formula (II-A) or the Intermediate of 3-substituted phenyl-5-Aminomethyl-isoxazole of Formula (II-B)

using substituted benzaldehyde as a raw material via oxime formation, 1,3-dipolar cycloaddition reaction, methylsulfonyl-esterification reaction, azidation and reduction to obtain the compound of formula (II-A) and formula (II-B) (R and n are as described above), as specifically described in the following scheme:

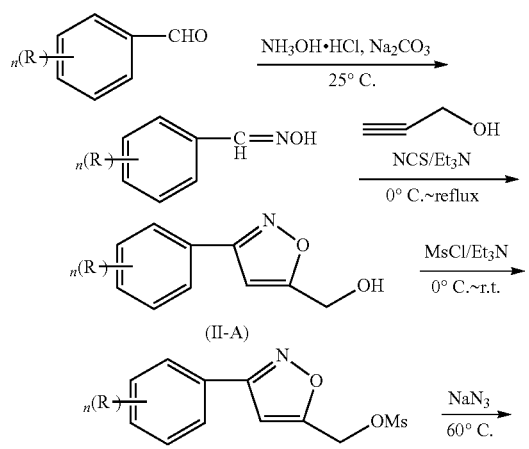

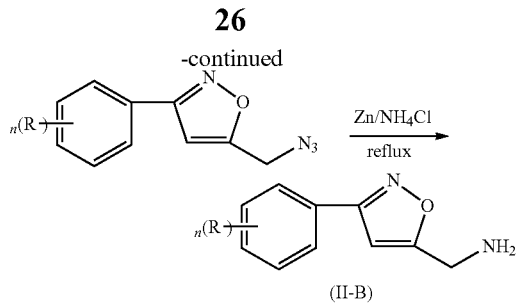

The specific synthesis processes for the intermediate of 3-substituted phenyl-5-hydroxymethyl-isoxazole of formula (II-A) or the intermediate of 3-substituted phenyl-5-aminomethyl-isoxazole of formula (II-B) are disclosed by the applicant in the publication numbers of the previous applications as CN103360382A, CN103664991A and CN103601762A, which is herein incorporated by reference in its entirety.

Example 2 the Synthesis of the Ferrocene Derivative Represented by Formula (IA) (Wherein Z Represents O.)

Wherein, the reaction of 1,1'-ferrocenedicarboxylic acid and 3-phenyl-5-hydroxymethyl-isoxazole is illustrated as an example:

the synthesis of the ferrocene-dicarboxylate derivative (YJP-1):

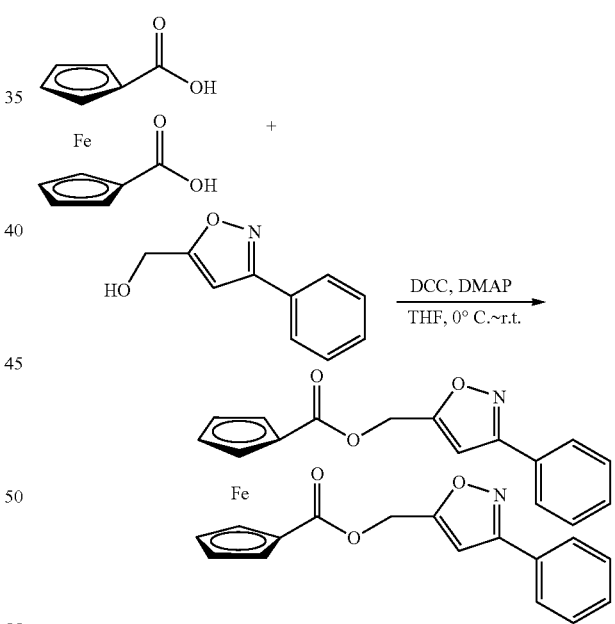

adding 1,1'-ferrocenedicarboxylic acid (0.274 g, 1 mmol) and DCC (0.412 g, 2 mmol) into a 50 mL round-bottom flask and adding 10 mL of dry THF; after stirring the solution in an ice bath for 30 minutes, slowly dropwise adding 10 mL THF solution of 3-phenyl-5-hydroxymethyl-isoxazole (0.35 g, 2 mmol) and DMAP (0.244 g, 2 mmol) into the reaction system; after stirring the reaction in an ice bath for 30 minutes, the reaction temperature being naturally increased to room temperature. When TLC detection showing that the reaction was complete, condensing the reaction solution under reduced pressure; directly separating the residue by using column chromatography (petroleum ether:ethyl acetate=5:1-2:1, volume ratio) to obtain the desired ferrocene-dicarboxylate derivative (YJP-1).

The rest of the ferrocene-dicarboxylate compounds represented by the formula (IA), when Z was O, were synthesized according to the synthetic process of the ferrocene-dicarboxylate derivative (YJP-1).

Example 3 the Synthesis of the Ferrocene Derivative Represented by Formula (IA) (Wherein Z Represents NH.)

Wherein, the reaction of 1,1'-ferrocenedicarboxylic acid and 3-phenyl-5-aminomethyl-isoxazole is illustrated as an example:
the synthesis of the ferrocene-dicarboxamide derivative (YJP-20):

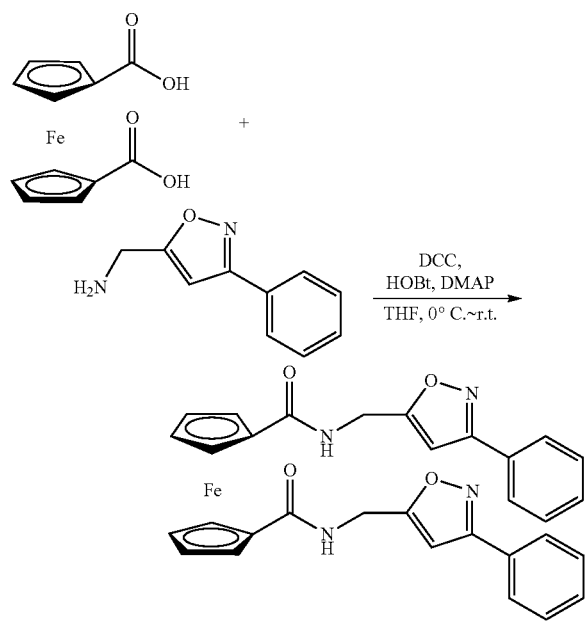

adding 1,1'-ferrocenedicarboxylic acid (0.274 g, 1 mmol), DCC (0.412 g, 2 mmol) and HOBt (0.270 g, 2 mmol) into a 50 mL round-bottom flask and adding 10 mL of dry THF; after stirring the solution in an ice bath for 30 minutes, slowly dropwise adding 10 mL THF solution of 3-phenyl-5-aminomethyl-isoxazole (0.348 g, 2 mmol) and DMAP (0.244 g, 2 mmol) into the reaction system; after stirring the reaction in an ice bath for 30 minutes, the reaction temperature being naturally increased to room temperature. When TLC detection showing that the reaction was complete, condensing the reaction solution under reduced pressure; directly separating the residue by using column chromatography (petroleum ether:ethyl acetate=5:1-2:1, volume ratio) to afford the desired ferrocenedicarboxamide derivative (YJP-20).

The rest of the ferrocene-dicarboxamide compounds were synthesized according to the synthetic process of the compound (YJP-20).

Example 4 the Synthesis of the Ferrocene Derivative Represented by Formula (IB) (Wherein Z Represents O.)

Wherein, the reaction of 1,1'-ferrocenedicarboxylic acid and 3-phenyl-5-hydroxymethyl-isoxazole is illustrated as an example:
the synthesis of the ferrocene derivative (YJP-41):

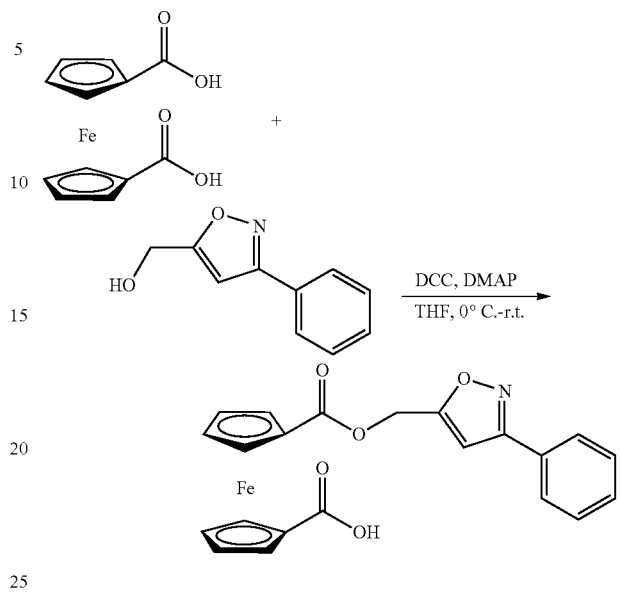

adding 1,1'-ferrocenedicarboxylic acid (0.274 g, 1 mmol) and DCC (0.206 g, 1 mmol) into a 50 mL round-bottom flask and adding 10 mL of dry THF; after stirring the solution in an ice bath for 30 minutes, slowly dropwise adding 10 mL THF solution of 3-phenyl-5-hydroxymethyl-isoxazole (0.125 g, 1 mmol) and DMAP (0.122 g, 1 mmol) into the reaction system; after stirring the reaction in an ice bath for 30 minutes, the reaction temperature being naturally increased to room temperature. When TLC detection showing that the reaction was complete, condensing the reaction solution under reduced pressure; directly separating the residue by using column chromatography (petroleum ether:ethyl acetate=5:1-0:1, volume ratio) to afford the desired ferrocene-dicarboxylate derivative (YJP-41).

The rest of the ferrocene-dicarboxylate derivatives were synthesized according to the synthetic process of the ferrocene derivative (YJP-41).

Example 5 the Synthesis of the Ferrocene Derivative Represented by Formula (IB) (Wherein Z Represents NH.)

Wherein, the reaction of 1,1'-ferrocenedicarboxylic acid and 3-phenyl-5-aminomethyl-isoxazole is illustrated as an example:
the synthesis of the ferrocene derivative (YJP-61):

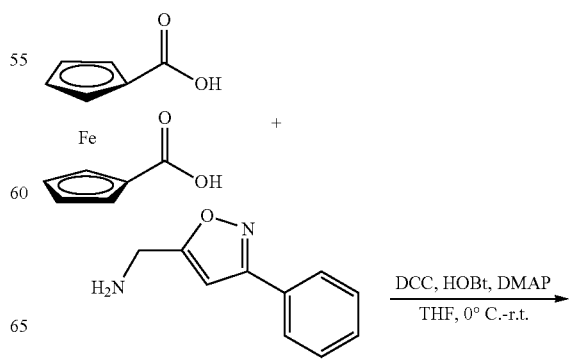

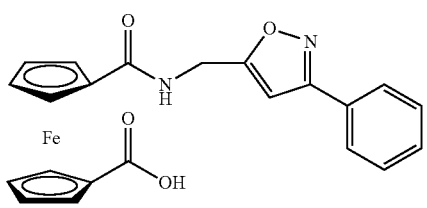

adding 1,1'-ferrocenedicarboxylic acid (0.274 g, 1 mmol), DCC (0.206 g, 1 mmol) and HOBt (0.135 g, 1 mmol) into a 50 mL round-bottom flask and adding 10 mL of dry THF; after stirring the solution in an ice bath for 30 minutes, slowly dropwise adding 10 mL THF solution of 3-phenyl-5-aminomethyl-isoxazole (0.174 g, 1 mmol) and DMAP (0.122 g, 1 mmol) into the reaction system; after stirring the reaction in an ice bath for 30 minutes, the reaction temperature being naturally increased to room temperature. When TLC detection showing that the reaction was complete, condensing the reaction solution under reduced pressure; directly separating the residue by using column chromatography (petroleum ether:ethyl acetate=5:1-2:1, volume ratio) to afford the desired ferrocene derivative (YJP-61).

The rest of the ferrocene derivatives represented by the formula (IB) were synthesized according to the synthetic process of the compound (YJP-61).

The structures were characterized by IR, $^1$H NMR, ESI-MS and other analytical methods. The physical constants and spectral data of preferred compounds are indicated in the tables.

The structures and numbers of the preferred compounds are as follows:

YJP-1

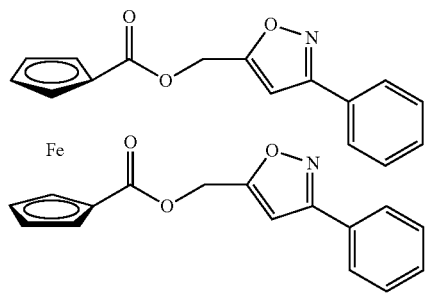

YJP-2

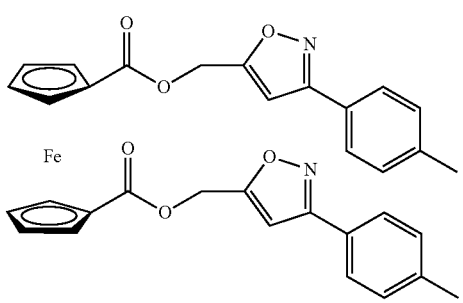

YJP-3

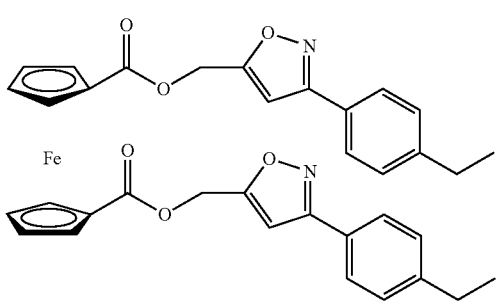

YJP-4

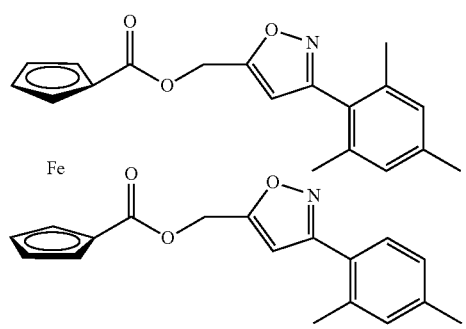

YJP-5

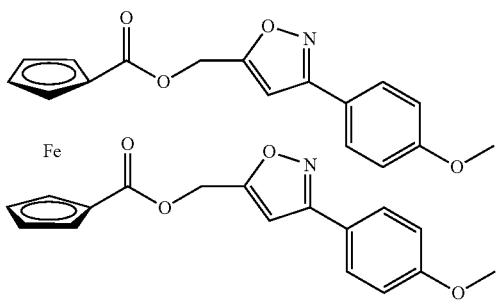

YJP-6

-continued
YJP-7
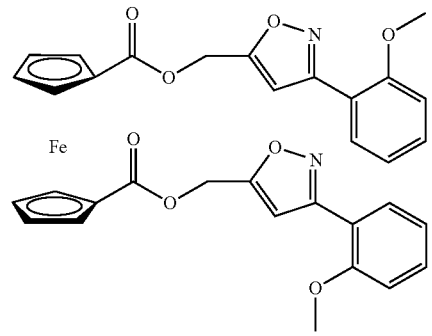
YJP-8
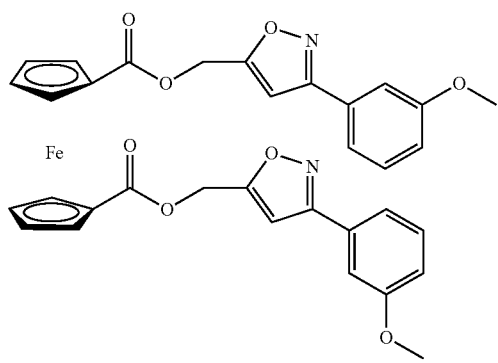
YJP-9
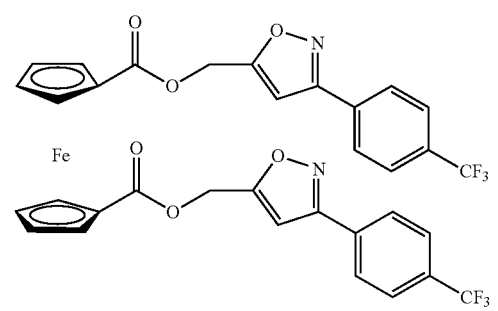
YJP-10
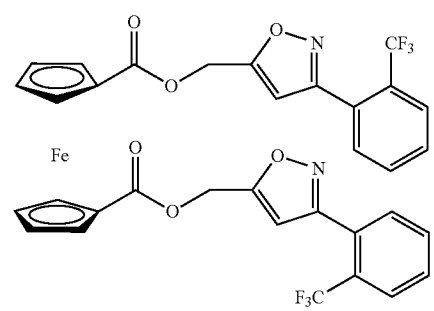
-continued
YJP-11
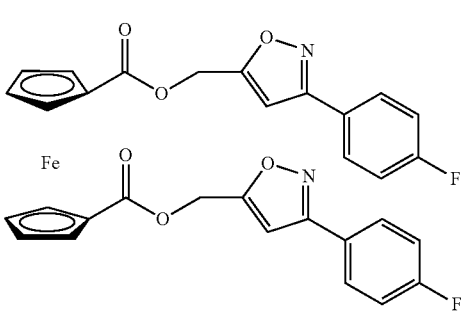
YJP-12
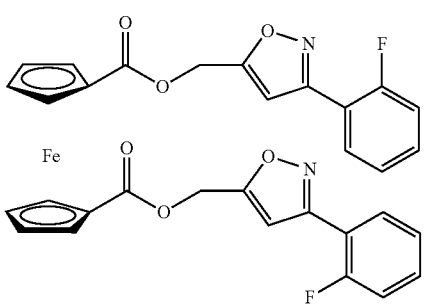
YJP-13
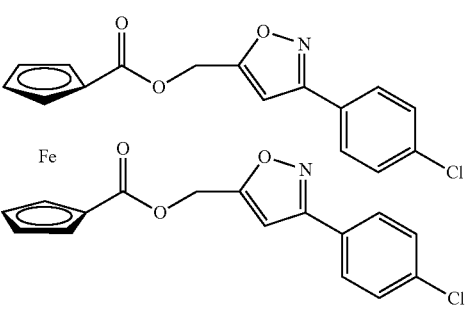
YJP-14
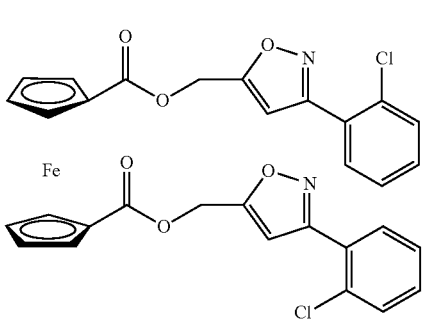
YJP-15
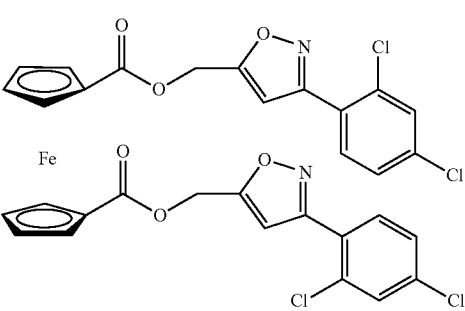

YJP-16
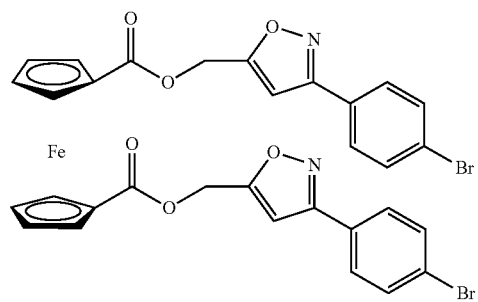
YJP-17
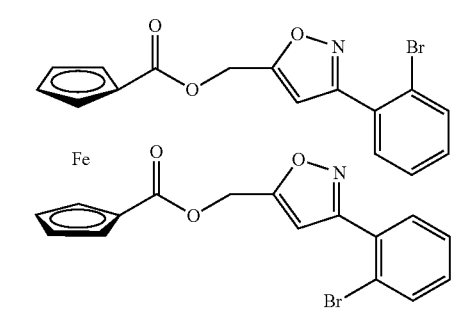
YJP-18
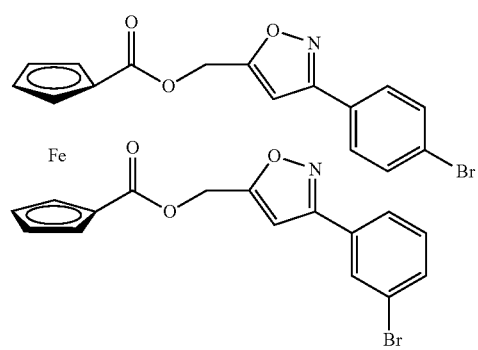
YJP-19
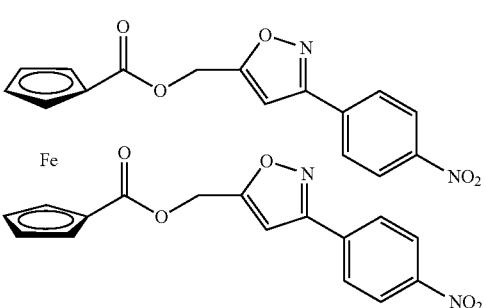
YJP-20
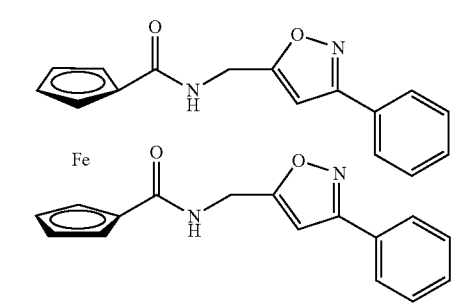
YJP-21
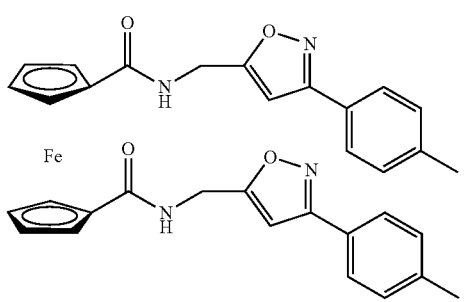
YJP-22
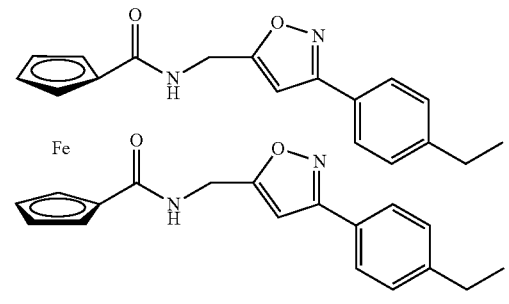
YJP-23
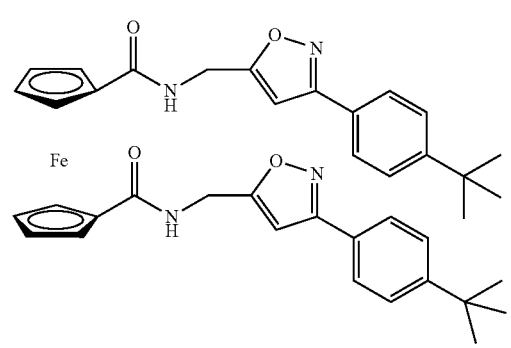
YJP-24
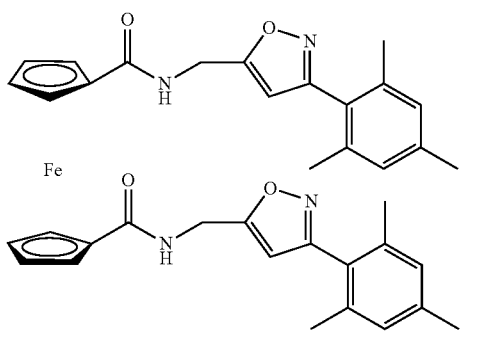
YJP-25
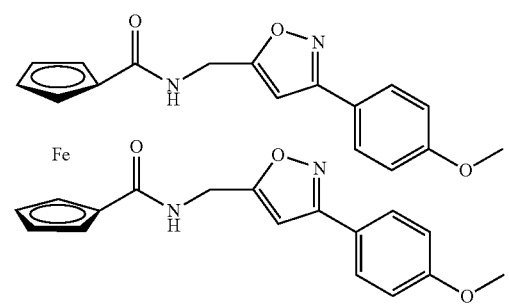

YJP-26
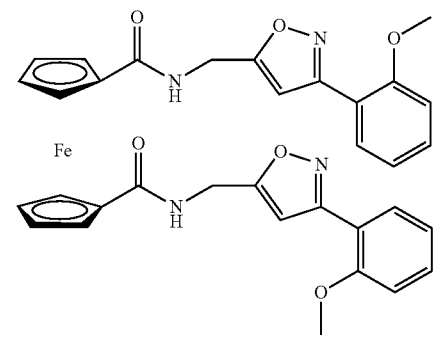
YJP-27
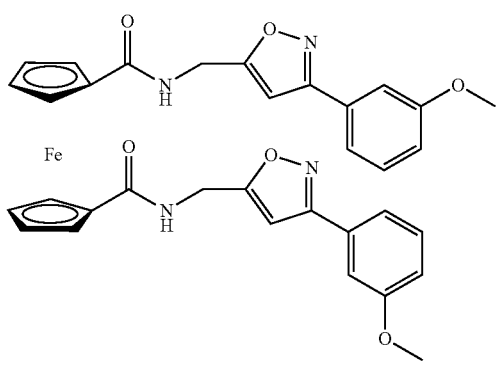
YJP-28
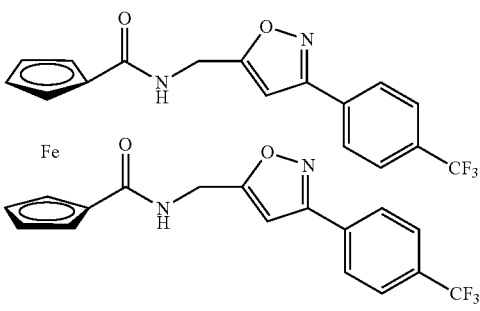
YJP-29
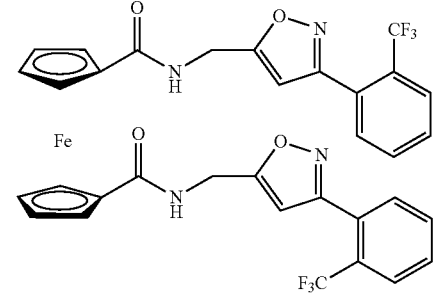
YJP-30
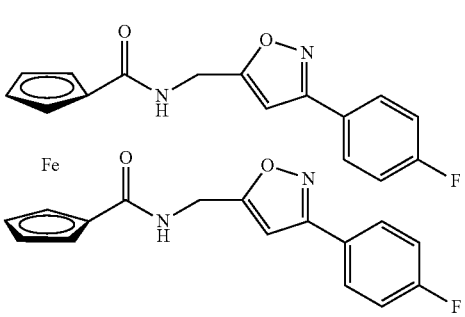
YJP-31
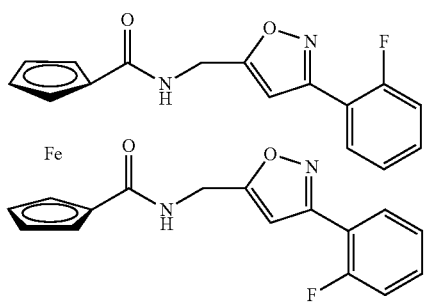
YJP-32
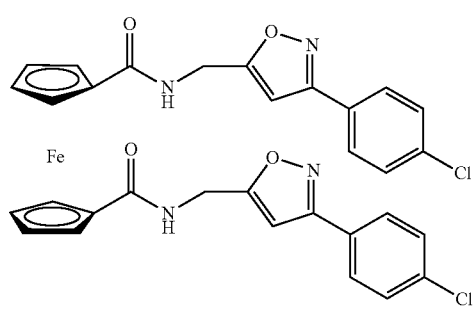
YJP-33
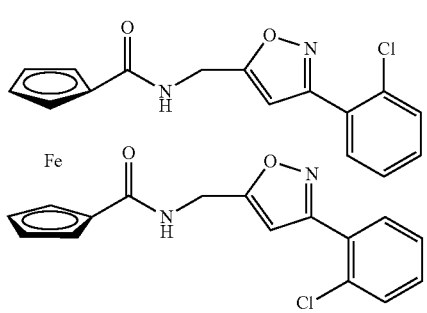
YJP-34
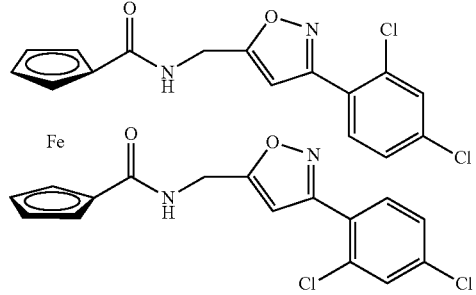
YJP-35
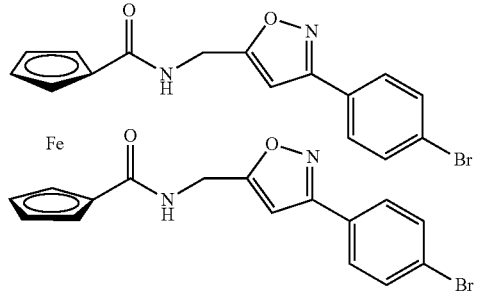

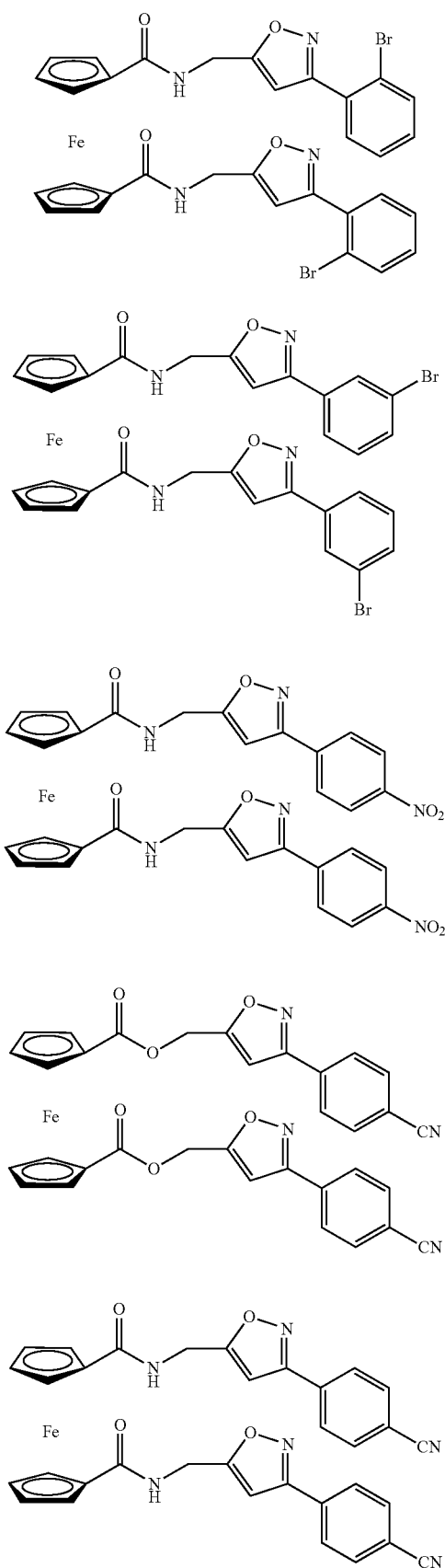
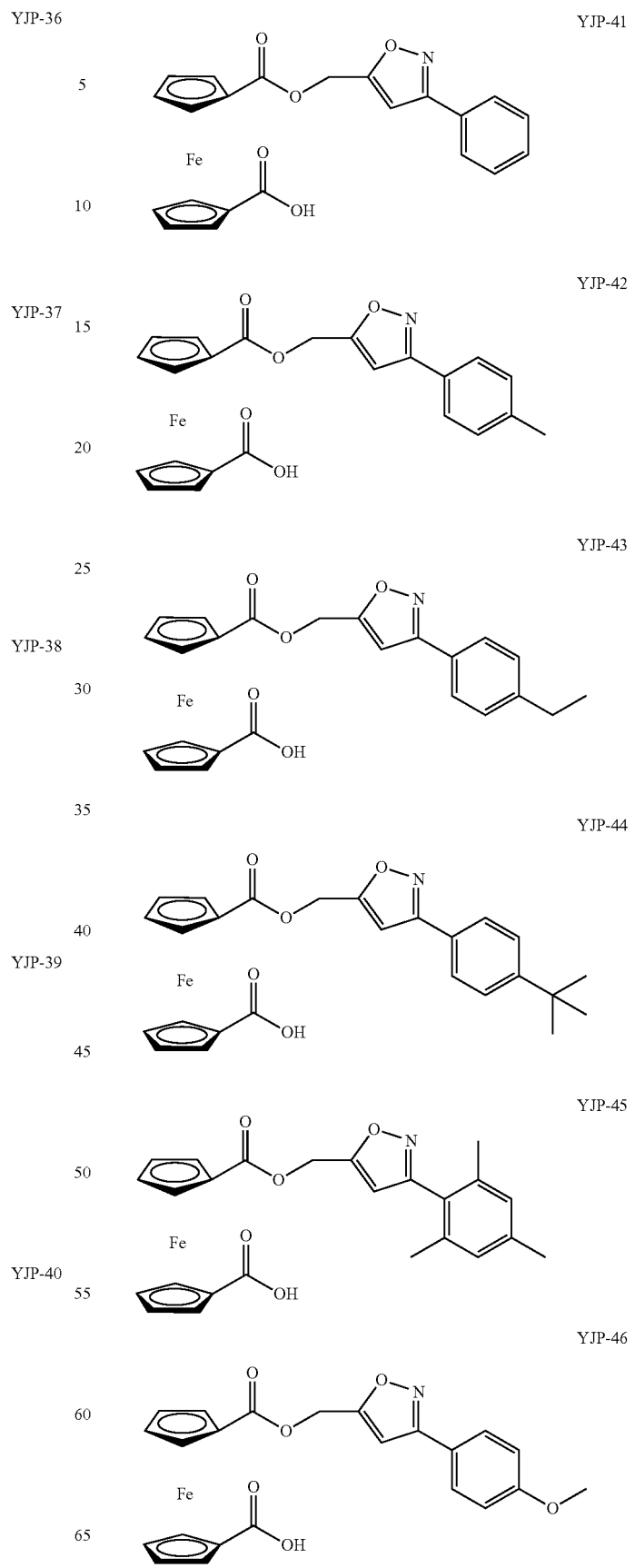

YJP-47
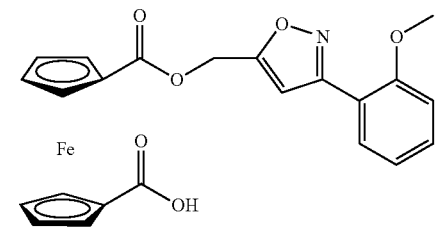
YJP-48
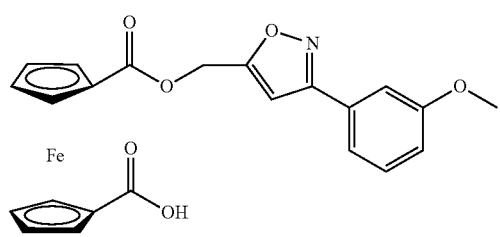
YJP-49
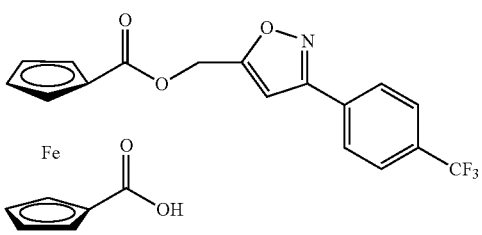
YJP-50
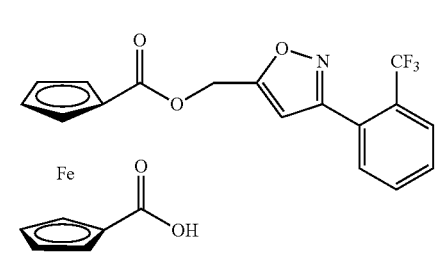
YJP-51
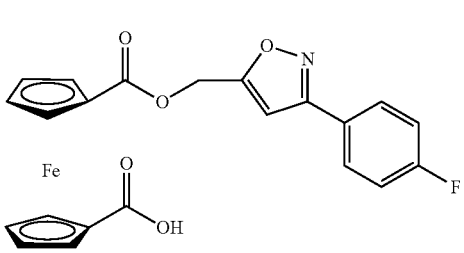
YJP-52
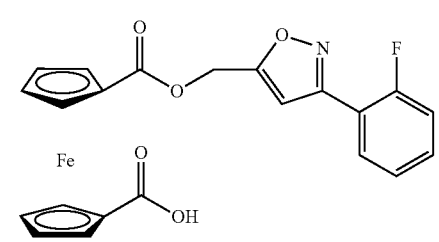
YJP-53
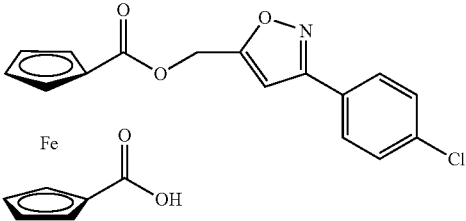
YJP-54
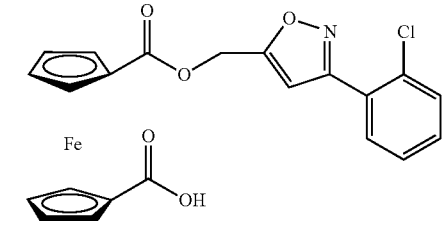
YJP-55
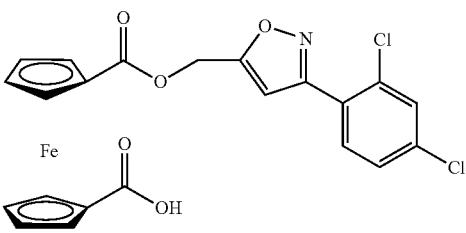
YJP-56
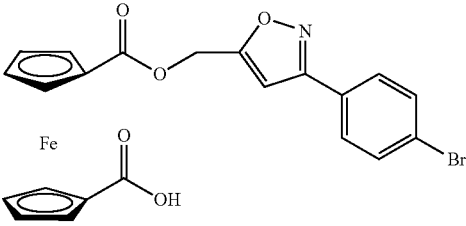
YJP-57
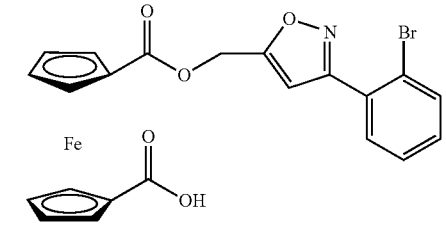
YJP-58
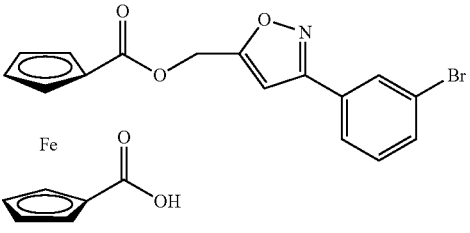
YJP-59
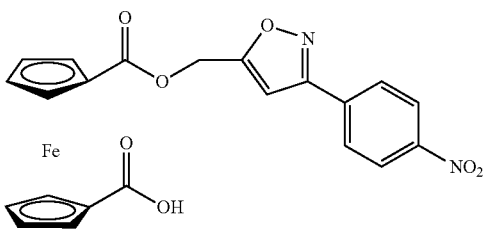

-continued
YJP-60
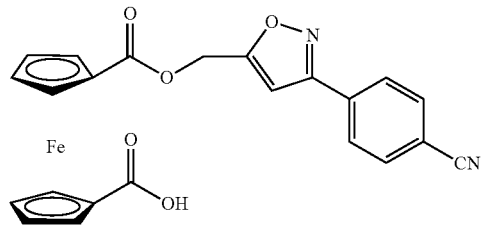
YJP-61
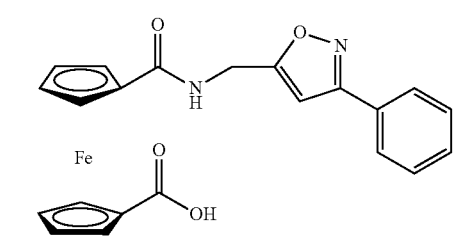
YJP-62
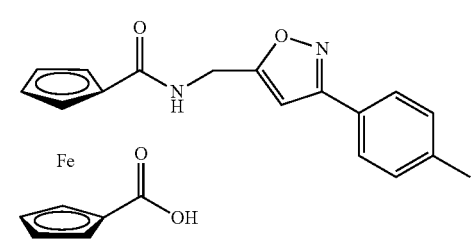
YJP-63
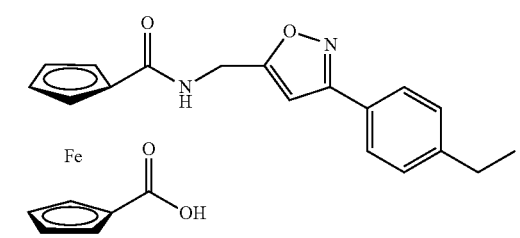
YJP-64
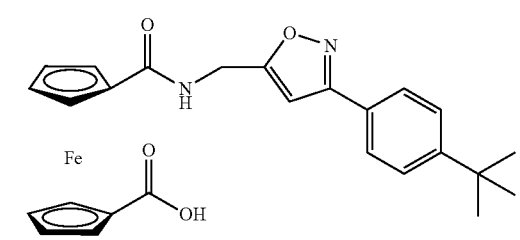
YJP-65
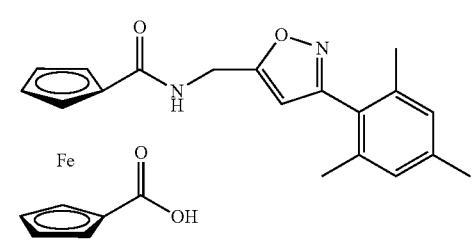
YJP-66
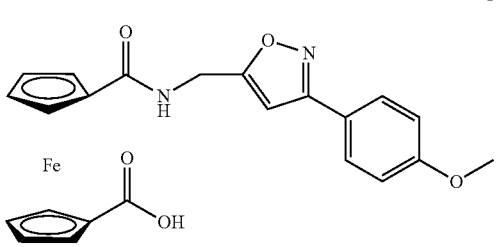
YJP-67
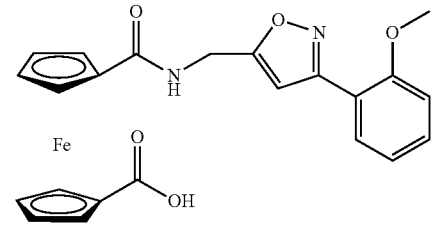
YJP-68
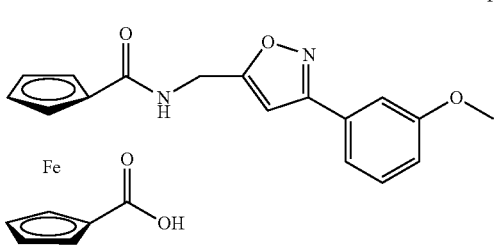
YJP-69
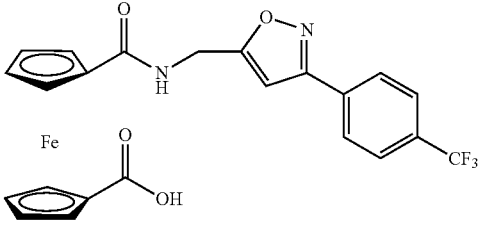
YJP-70
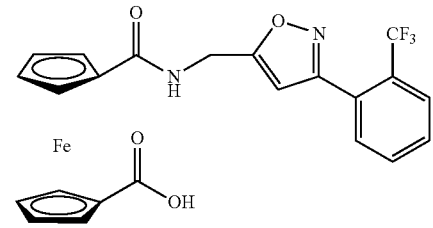
YJP-71
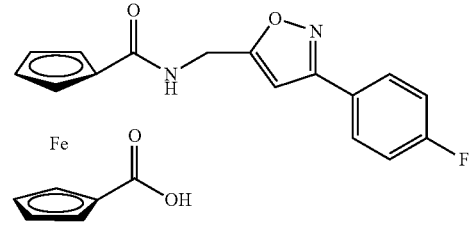

-continued

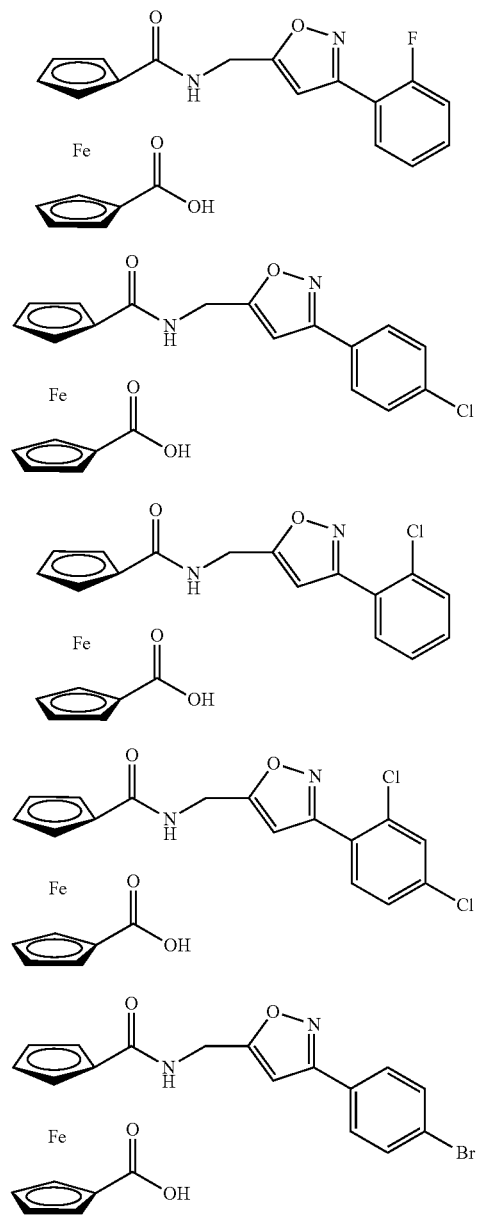

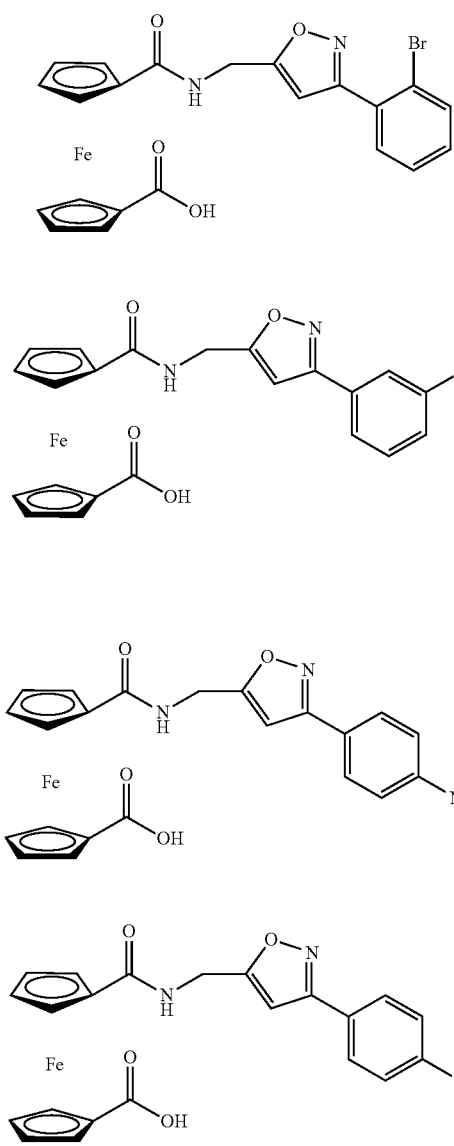

The numbers and the physical constants of the preferred compounds are shown as follows:

TABLE 1

$^1$H NMR data of the preferred compounds

Number $^1$H NMR (400 MHz, CDCl$_3$)

YJP-1  4.47 (2 × 2H, t, J = 2.0 Hz), 4.88 (2 × 2H, t, J = 1.6 Hz), 5.41 (s, 4H, 2 × CH$_2$ of isoxazole-CH$_2$), 6.73 (s, 2H, 2 × 1H of isoxazole), 7.47-7.49 (m, 2 × 3H), 7.83-7.86 (m, 2 × 2H).

YJP-2  2.42 (s, 6H, 2 × CH$_3$), 4.46 (2 × 2H, t, J = 2.0 Hz), 4.88 (2 × 2H, t, J = 2.0 Hz), 5.40 (s, 4H, 2 × CH$_2$ of isoxazole-CH$_2$), 6.70 (s, 2H, 2 × 1H of isoxazole), 7.28 (2 × 2H, d, J = 4.8 Hz), 7.74 (2 × 2H, d, J = 8.0 Hz).

YJP-3  1.29 (6H, 2 × CH$_3$, t, J = 7.6 Hz), 2.72 (4H, 2 × CH$_2$, q, J = 7.6 Hz), 4.46 (2 × 2H, t, J = 2.0 Hz), 4.88 (2 × 2H, t, J = 2.0 Hz), 5.40 (s, 4H, 2 × CH$_2$ of isoxazole-CH$_2$), 6.70 (s, 2H, 2 × 1H of isoxazole), 7.32 (2 × 2H, d, J = 8.0 Hz), 7.74 (2 × 2H, d, J = 8.4 Hz).

YJP-4  1.37 (s, 18H, 2 × 3CH$_3$), 4.46 (2 × 2H, t, J = 2.0 Hz), 4.88 (2 × 2H, t, J = 2.0 Hz), 5.40 (s, 4H, 2 × CH$_2$ of isoxazole-CH$_2$), 6.71 (s, 2H, 2 × 1H of isoxazole), 7.51 (2 × 2H, d, J = 8.4 Hz), 7.78 (2 × 2H, d, J = 6.8 Hz).

YJP-5  2.17 (s, 12H, 4 × CH$_3$), 2.34 (s, 6H, 2 × CH$_3$), 4.47 (2 × 2H, t, J = 2.0 Hz), 4.89 (2 × 2H, t, J = 2.0 Hz), 5.43 (s, 4H, 2 × CH$_2$ of isoxazole-CH$_2$), 6.71 (s, 2H, 2 × 1H of isoxazole), 6.96 (s, 2 × 2H).

TABLE 1-continued

¹H NMR data of the preferred compounds

Number ¹H NMR (400 MHz, CDCl₃)

YJP-6  3.88 (s, 6H, 2 × OCH₃), 4.47 (2 × 2H, t, J = 2.0 Hz), 4.88 (2 × 2H, t, J = 2.0 Hz), 5.39 (s, 4H, 2 × CH₂ of isoxazole-CH₂), 6.67 (s, 2H, 2 × 1H of isoxazole), 7.00 (d, 2 × 2H, J = 5.2 Hz), 7.79 (d, 2 × 2H, J = 9.2 Hz).

YJP-7  3.92 (s, 6H, 2 × OCH₃), 4.46 (2 × 2H, t, J = 2.0 Hz), 4.88 (2 × 2H, t, J = 2.0 Hz), 5.41 (s, 4H, 2 × CH₂ of isoxazole-CH₂), 6.92 (s, 2H, 2 × 1H of isoxazole), 7.01-7.08 (m, 2 × 2H), 7.42-7.46 (m, 2 × 1H), 7.91 (2 × 1H, dd, J = 1.6, 2.0 Hz).

YJP-8  3.89 (s, 6H, 2 × OCH₃), 4.47 (2 × 2H, t, J = 2.0 Hz), 4.88 (2 × 2H, t, J = 2.0 Hz), 5.40 (s, 4H, 2 × CH₂ of isoxazole-CH₂), 6.71 (s, 2H, 2 × 1H of isoxazole), 7.00-7.04 (m, 2 × 1H), 7.38-7.41 (m, 2 × 3H).

YJP-9  4.47 (2 × 2H, t, J = 2.0 Hz), 4.88 (2 × 2H, t, J = 2.0 Hz), 5.42 (s, 4H, 2 × CH₂ of isoxazole-CH₂), 6.71 (s, 2H, 2 × 1H of isoxazole), 7.76 (2 × 2H, d, J = 8.4 Hz), 7.98 (2 × 2H, d, J = 8.4 Hz).

YJP-10  3.92 (s, 6H, 2 × OCH₃), 4.46 (2 × 2H, t, J = 2.0 Hz), 4.88 (2 × 2H, t, J = 2.0 Hz), 5.41 (s, 4H, 2 × CH₂ of isoxazole-CH₂), 6.92 (s, 2H, 2 × 1H of isoxazole), 7.01-7.08 (m, 2 × 2H), 7.42-7.46 (m, 2 × 1H), 7.91 (2 × 1H, dd, J = 1.6, 2.0 Hz).

YJP-11  4.47 (2 × 2H, t, J = 2.0 Hz), 4.88 (2 × 2H, t, J = 2.0 Hz), 5.40 (s, 4H, 2 × CH₂ of isoxazole-CH₂), 6.69 (s, 2H, 2 × 1H of isoxazole), 7.20 (2 × 2H, d, J = 8.8 Hz), 7.85 (2 × 2H, d, J = 8.8 Hz).

YJP-12  4.47 (2 × 2H, t, J = 2.0 Hz), 4.88 (2 × 2H, t, J = 2.0 Hz), 5.42 (s, 4H, 2 × CH₂ of isoxazole-CH₂), 6.87 (s, 2H, 2 × 1H of isoxazole), 7.18-7.26 (m, 2 × 2H), 7.43-7.49 (m, 2 × 1H), 7.99-8.04 (m, 2 × 1H).

YJP-13  4.47 (2 × 2H, t, J = 2.0 Hz), 4.88 (2 × 2H, t, J = 2.0 Hz), 5.40 (s, 4H, 2 × CH₂ of isoxazole-CH₂), 6.70 (s, 2H, 2 × 1H of isoxazole), 7.47 (2 × 2H, d, J = 8.8 Hz), 7.79 (2 × 2H, d, J = 8.8 Hz).

YJP-14  4.47 (2 × 2H, t, J = 2.0 Hz), 4.88 (2 × 2H, t, J = 2.0 Hz), 5.43 (s, 4H, 2 × CH₂ of isoxazole-CH₂), 6.90 (s, 2H, 2 × 1H of isoxazole), 7.35-7.44 (m, 2 × 2H), 7.52 (dd, 2 × 1H, J = 1.2, 1.2 Hz), 7.77 (dd, 2 × 1H, J = 2.0, 2.0 Hz).

YJP-15  4.47 (2 × 2H, t, J = 2.0 Hz), 4.88 (2 × 2H, t, J = 2.0 Hz), 5.42 (s, 4H, 2 × CH₂ of isoxazole-CH₂), 6.89 (s, 2H, 2 × 1H of isoxazole), 7.37 (dd, 2 × 1H, J = 2.0, 2.0 Hz), 7.54 (2 × 1H, d, J = 2.0 Hz), 7.73 (2 × 1H, d, J = 8.4 Hz).

YJP-16  4.47 (2 × 2H, t, J = 2.0 Hz), 4.88 (2 × 2H, t, J = 2.0 Hz), 5.40 (s, 4H, 2 × CH₂ of isoxazole-CH₂), 6.70 (s, 2H, 2 × 1H of isoxazole), 7.63 (2 × 2H, d, J = 8.8 Hz), 7.79 (2 × 2H, d, J = 8.4 Hz).

YJP-17  4.47 (2 × 2H, t, J = 2.0 Hz), 4.88 (2 × 2H, t, J = 2.0 Hz), 5.42 (s, 4H, 2 × CH₂ of isoxazole-CH₂), 6.87 (s, 2H, 2 × 1H of isoxazole), 7.18-7.26 (m, 2 × 2H), 7.43-7.49 (m, 2 × 1H), 7.99-8.04 (m, 2 × 1H).

YJP-18  4.47 (2 × 2H, t, J = 2.0 Hz), 4.88 (2 × 2H, t, J = 2.0 Hz), 5.40 (s, 4H, 2 × CH₂ of isoxazole-CH₂), 6.71 (s, 2H, 2 × 1H of isoxazole), 7.00-7.04 (m, 2 × 1H), 7.38-7.41 (m, 2 × 3H).

YJP-19  4.48 (2 × 2H, t, J = 2.0 Hz), 4.88 (2 × 2H, t, J = 2.0 Hz), 5.43 (s, 4H, 2 × CH₂ of isoxazole-CH₂), 6.80 (s, 2H, 2 × 1H of isoxazole), 8.04 (2 × 2H, d, J = 8.8 Hz), 7.79 (2 × 2H, d, J = 8.4 Hz).

YJP-20  4.47 (2 × 2H, t, J = 2.0 Hz), 4.88 (2 × 2H, t, J = 1.6 Hz), 5.41 (s, 4H, 2 × CH₂ of isoxazole-CH₂), 5.66 (2H, t, 2 × NH—CO—, J = 4.6 Hz), 6.73 (s, 2H, 2 × 1H of isoxazole), 7.47-7.49 (m, 2 × 3H), 7.83-7.86 (m, 2 × 2H).

YJP-21  2.42 (s, 6H, 2 × CH₃), 4.46 (2 × 2H, t, J = 2.0 Hz), 4.88 (2 × 2H, t, J = 2.0 Hz), 5.40 (s, 4H, 2 × CH₂ of isoxazole-CH₂), 5.66 (2H, t, 2 × NH—CO—, J = 4.6 Hz), 6.70 (s, 2H, 2 × 1H of isoxazole), 7.28 (2 × 2H, d, J = 4.8 Hz), 7.74 (2 × 2H, d, J = 8.0 Hz).

YJP-22  1.29 (6H, 2 × CH₃, t, J = 7.6 Hz), 2.72 (4H, 2 × CH₂, q, J = 7.6 Hz), 4.46 (2 × 2H, t, J = 2.0 Hz), 4.88 (2 × 2H, t, J = 2.0 Hz), 5.40 (s, 4H, 2 × CH₂ of isoxazole-CH₂), 5.66 (2H, t, 2 × NH—CO—, J = 4.6 Hz), 6.70 (s, 2H, 2 × 1H of isoxazole), 7.32 (2 × 2H, d, J = 8.0 Hz), 7.74 (2 × 2H, d, J = 8.4 Hz).

YJP-23  1.37 (s, 18H, 6 × CH₃), 4.46 (2 × 2H, t, J = 2.0 Hz), 4.88 (2 × 2H, t, J = 2.0 Hz), 5.40 (s, 4H, 2 × CH₂ of isoxazole-CH₂), 5.66 (2H, t, 2 × NH—CO—, J = 4.6 Hz), 6.71 (s, 2H, 2 × 1H of isoxazole), 7.51 (2 × 2H, d, J = 8.4 Hz), 7.78 (2 × 2H, d, J = 6.8 Hz).

YJP-24  2.17 (s, 12H, 4 × CH₃), 2.34 (s, 6H, 2 × CH₃), 4.47 (2 × 2H, t, J = 2.0 Hz), 4.89 (2 × 2H, t, J = 2.0 Hz), 5.43 (s, 4H, 2 × CH₂ of isoxazole-CH₂), 5.66 (2H, t, 2 × NH—CO—, J = 4.6 Hz), 6.71 (s, 2H, 2 × 1H of isoxazole), 6.96 (s, 2 × 2H).

YJP-25  3.88 (s, 6H, 2 × OCH₃), 4.47 (2 × 2H, t, J = 2.0 Hz), 4.88 (2 × 2H, t, J = 2.0 Hz), 5.39 (s, 4H, 2 × CH₂ of isoxazole-CH₂), 5.66 (2H, t, 2 × NH—CO—, J = 4.6 Hz), 6.67 (s, 2H, 2 × 1H of isoxazole), 7.00 (d, 2 × 2H, J = 5.2 Hz), 7.79 (d, 2 × 2H, J = 9.2 Hz).

YJP-26  3.92 (s, 6H, 2 × OCH₃), 4.46 (2 × 2H, t, J = 2.0 Hz), 4.88 (2 × 2H, t, J = 2.0 Hz), 5.41 (s, 4H, 2 × CH₂ of isoxazole-CH₂), 5.66 (2H, t, 2 × NH—CO—, J = 4.6 Hz), 6.92 (s, 2H, 2 × 1H of isoxazole), 7.01-7.08 (m, 2 × 2H), 7.42-7.46 (m, 2 × 1H), 7.91 (2 × 1H, dd, J = 1.6, 2.0 Hz).

YJP-27  3.89 (s, 6H, 2 × OCH₃), 4.47 (2 × 2H, t, J = 2.0 Hz), 4.88 (2 × 2H, t, J = 2.0 Hz), 5.40 (s, 4H, 2 × CH₂ of isoxazole-CH₂), 5.66 (2H, t, 2 × NH—CO—, J = 4.6 Hz), 6.71 (s, 2H, 2 × 1H of isoxazole), 7.00-7.04 (m, 2 × 1H), 7.38-7.41 (m, 2 × 3H).

YJP-28  4.47 (2 × 2H, t, J = 2.0 Hz), 4.88 (2 × 2H, t, J = 2.0 Hz), 5.42 (s, 4H, 2 × CH₂ of isoxazole-CH₂), 5.66 (2H, t, 2 × NH—CO—, J = 4.6 Hz), 6.71 (s, 2H, 2 × 1H of isoxazole), 7.76 (2 × 2H, d, J = 8.4 Hz), 7.98 (2 × 2H, d, J = 8.4 Hz).

YJP-29  4.46 (2 × 2H, t, J = 2.0 Hz), 4.88 (2 × 2H, t, J = 2.0 Hz), 5.41 (s, 4H, 2 × CH₂ of isoxazole-CH₂), 5.66 (2H, t, 2 × NH—CO—, J = 4.6 Hz), 6.92 (s, 2H, 2 × 1H of isoxazole), 7.01-7.08 (m, 2 × 2H), 7.42-7.46 (m, 2 × 1H), 7.91 (2 × 1H, dd, J = 1.6, 2.0 Hz).

YJP-30  4.47 (2 × 2H, t, J = 2.0 Hz), 4.88 (2 × 2H, t, J = 2.0 Hz), 5.40 (s, 4H, 2 × CH₂ of isoxazole-CH₂), 5.66 (2H, t, 2 × NH—CO—, J = 4.6 Hz), 6.69 (s, 2H, 2 × 1H of isoxazole), 7.20 (2 × 2H, d, J = 8.8 Hz), 7.85 (2 × 2H, d, J = 8.8 Hz).

TABLE 1-continued

¹H NMR data of the preferred compounds

Number ¹H NMR (400 MHz, CDCl₃)

YJP-31  4.47 (2 × 2H, t, J = 2.0 Hz), 4.88 (2 × 2H, t, J = 2.0 Hz), 5.42 (s, 4H, 2 × CH₂ of isoxazole-CH₂), 5.66 (2H, t, 2 × NH—CO—, J = 4.6 Hz), 6.87 (s, 2H, 2 × 1H of isoxazole), 7.18-7.26 (m, 2 × 2H), 7.43-7.49 (m, 2 × 1H), 7.99-8.04 (m, 2 × 1H).

YJP-32  4.47 (2 × 2H, t, J = 2.0 Hz), 4.88 (2 × 2H, t, J = 2.0 Hz), 5.40 (s, 4H, 2 × CH₂ of isoxazole-CH₂), 5.66 (2H, t, 2 × NH—CO—, J = 4.6 Hz), 6.70 (s, 2H, 2 × 1H of isoxazole), 7.47 (2 × 2H, d, J = 8.8 Hz), 7.79 (2 × 2H, d, J = 8.8 Hz).

YJP-33  4.47 (2 × 2H, t, J = 2.0 Hz), 4.88 (2 × 2H, t, J = 2.0 Hz), 5.43 (s, 4H, 2 × CH₂ of isoxazole-CH₂), 5.66 (2H, t, 2 × NH—CO—, J = 4.6 Hz), 6.90 (s, 2H, 2 × 1H of isoxazole), 7.35-7.44 (m, 2 × 2H), 7.52 (dd, 2 × 1H, J = 1.2, 1.2 Hz), 7.77 (dd, 2 × 1H, J = 2.0 , 2.0 Hz).

YJP-34  4.47 (2 × 2H, t, J = 2.0 Hz), 4.88 (2 × 2H, t, J = 2.0 Hz), 5.42 (s, 4H, 2 × CH₂ of isoxazole-CH₂), 5.66 (2H, t, 2 × NH—CO—, J = 4.6 Hz), 6.89 (s, 2H, 2 × 1H of isoxazole), 7.37 (dd, 2 × 1H, J = 2.0 , 2.0 Hz), 7.54 (2 × 1H, d, J = 2.0 Hz), 7.73 (2 × 1H, d, J = 8.4 Hz).

YJP-35  4.47 (2 × 2H, t, J = 2.0 Hz), 4.88 (2 × 2H, t, J = 2.0 Hz), 5.40 (s, 4H, 2 × CH₂ of isoxazole-CH₂), 5.66 (2H, t, 2 × NH—CO—, J = 4.6 Hz), 6.70 (s, 2H, 2 × 1H of isoxazole), 7.63 (2 × 2H, d, J = 8.8 Hz), 7.79 (2 × 2H, d, J = 8.4 Hz).

YJP-36  4.47 (2 × 2H, t, J = 2.0 Hz), 4.88 (2 × 2H, t, J = 2.0 Hz), 5.42 (s, 4H, 2 × CH₂ of isoxazole-CH₂), 5.66 (2H, t, 2 × NH—CO—, J = 4.6 Hz), 6.87 (s, 2H, 2 × 1H of isoxazole), 7.18-7.26 (m, 2 × 2H), 7.43-7.49 (m, 2 × 1H), 7.99-8.04 (m, 2 × 1H).

YJP-37  4.47 (2 × 2H, t, J = 2.0 Hz), 4.88 (2 × 2H, t, J = 2.0 Hz), 5.40 (s, 4H, 2 × CH₂ of isoxazole-CH₂), 5.66 (2H, t, 2 × NH—CO—, J = 4.6 Hz), 6.71 (s, 2H, 2 × 1H of isoxazole), 7.00-7.04 (m, 2 × 1H), 7.38-7.41 (m, 2 × 3H).

YJP-38  4.48 (2 × 2H, t, J = 2.0 Hz), 4.88 (2 × 2H, t, J = 2.0 Hz), 5.43 (s, 4H, 2 × CH₂ of isoxazole-CH₂), 5.66 (2H, t, 2 × NH—CO—, J = 4.6 Hz), 6.80 (s, 2H, 2 × 1H of isoxazole), 8.04 (2 × 2H, d, J = 8.8 Hz), 7.79 (2 × 2H, d, J = 8.4 Hz).

YJP-39  4.47 (2 × 2H, t, J = 2.0 Hz), 4.88 (2 × 2H, t, J = 2.0 Hz), 5.40 (s, 4H, 2 × CH₂ of isoxazole-CH₂), 6.70 (s, 2H, 2 × 1H of isoxazole), 7.63 (2 × 2H, d, J = 8.8 Hz), 7.79 (2 × 2H, d, J = 8.4 Hz).

YJP-40  4.48 (2 × 2H, t, J = 2.0 Hz), 4.88 (2 × 2H, t, J = 2.0 Hz), 5.43 (s, 4H, 2 × CH₂ of isoxazole-CH₂), 5.66 (2H, t, 2 × NH—CO—, J = 4.6 Hz), 6.80 (s, 2H, 2 × 1H of isoxazole), 8.04 (2 × 2H, d, J = 8.8 Hz), 7.79 (2 × 2H, d, J = 8.4 Hz).

YJP-41  4.47 (2 × 2H, t, J = 2.0 Hz), 4.88 (2 × 2H, t, J = 1.6 Hz), 5.41 (s, 2H, isoxazole-CH₂), 6.73 (s, 1H, 1H of isoxazole), 7.47-7.49 (m, 3H), 7.83-7.86 (m, 2H), 10.8 (brs, 1H, —COOH).

YJP-42  2.42 (s, 3H, CH₃), 4.46 (2 × 2H, t, J = 2.0 Hz), 4.88 (2 × 2H, t, J = 2.0 Hz), 5.40 (s, 2H, isoxazole-CH₂), 6.70 (s, 1H, 1H of isoxazole), 7.28 (2H, d, J = 4.8 Hz), 7.74 (2H, d, J = 8.0 Hz), 10.8 (brs, 1H, —COOH).

YJP-43  1.29 (3H, CH₃, t, J = 7.6 Hz), 2.72 (2H, CH₃CH₂, q, J = 7.6 Hz), 4.46 (2 × 2H, t, J = 2.0 Hz), 4.88 (2 × 2H, t, J = 2.0 Hz), 5.40 (s, 2H, isoxazole-CH₂), 6.70 (s, 1H, 1H of isoxazole), 7.32 (2H, d, J = 8.0 Hz), 7.74 (2H, d, J = 8.4 Hz), 11.0 (brs, 1H, —COOH).

YJP-44  1.37 (s, 9H, 3 × CH₃), 4.46 (2 × 2H, t, J = 2.0 Hz), 4.88 (2 × 2H, t, J = 2.0 Hz), 5.40 (s, 2H, isoxazole-CH₂), 6.71 (s, 1H, 1H of isoxazole), 7.51 (2H, d, J = 8.4 Hz), 7.78 (2H, d, J = 6.8 Hz), 11.0 (brs, 1H, —COOH).

YJP-45  2.17 (s, 6H, 2 × CH₃), 2.34 (s, 3H, CH₃), 4.47 (2 × 2H, t, J = 2.0 Hz), 4.89 (2 × 2H, t, J = 2.0 Hz), 5.43 (s, 2H, isoxazole-CH₂), 6.71 (s, H, 1H of isoxazole), 6.96 (s, 2H), 11.0 (brs, 1H, —COOH).

YJP-46  3.88 (s, 3H, OCH₃), 4.47 (2 × 2H, t, J = 2.0 Hz), 4.88 (2 × 2H, t, J = 2.0 Hz), 5.39 (s, 2H, isoxazole-CH₂), 6.67 (s, 1H, 1H of isoxazole), 7.00 (d, 2H, J = 5.2 Hz), 7.79 (d, 2H, J = 9.2 Hz), 11.0 (brs, 1H, —COOH).

YJP-47  3.92 (s, 3H, OCH₃), 4.46 (2 × 2H, t, J = 2.0 Hz), 4.88 (2 × 2H, t, J = 2.0 Hz), 5.41 (s, 2H, isoxazole-CH₂), 6.92 (s, 1H, 1H of isoxazole), 7.01-7.08 (m, 2H), 7.42-7.46 (m, 1H), 7.91 (1H, dd, J = 1.6, 2.0 Hz), 11.0 (brs, 1H, —COOH).

YJP-48  3.89 (s, 3H, OCH₃), 4.47 (2 × 2H, t, J = 2.0 Hz), 4.88 (2 × 2H, t, J = 2.0 Hz), 5.40 (s, 2H, isoxazole-CH₂), 6.71 (s, 1H, 1H of isoxazole), 7.00-7.04 (m, 1H), 7.38-7.41 (m, 3H), 11.0 (brs, 1H, —COOH).

YJP-49  4.47 (2 × 2H, t, J = 2.0 Hz), 4.88 (2 × 2H, t, J = 2.0 Hz), 5.42 (s, 2H, isoxazole-CH₂), 6.71 (s, 1H, 1H of isoxazole), 7.76 (2H, d, J = 8.4 Hz), 7.98 (2H, d, J = 8.4 Hz), 11.0 (brs, 1H, —COOH).

YJP-50  3.92 (s, 3H, OCH₃), 4.46 (2 × 2H, t, J = 2.0 Hz), 4.88 (2 × 2H, t, J = 2.0 Hz), 5.41 (s, 2H, isoxazole-CH₂), 6.92 (s, 1H, 1H of isoxazole), 7.01-7.08 (m, 2H), 7.42-7.46 (m, 1H), 7.91 (1H, dd, J = 1.6, 2.0 Hz), 11.0 (brs, 1H, —COOH).

YJP-51  4.47 (2 × 2H, t, J = 2.0 Hz), 4.88 (2 × 2H, t, J = 2.0 Hz), 5.40 (s, 2H, isoxazole-CH₂), 6.69 (s, 1H, 1H of isoxazole), 7.20 (2H, d, J = 8.8 Hz), 7.85 (2H, d, J = 8.8 Hz), 11.0 (brs, 1H, —COOH).

YJP-52  4.47 (2 × 2H, t, J = 2.0 Hz), 4.88 (2 × 2H, t, J = 2.0 Hz), 5.42 (s, 2H, isoxazole-CH₂), 6.87 (s, 1H, 1H of isoxazole), 7.18-7.26 (m, 2H), 7.43-7.49 (m, 1H), 7.99-8.04 (m, 1H), 11.0 (brs, 1H, —COOH).

YJP-53  4.47 (2 × 2H, t, J = 2.0 Hz), 4.88 (2 × 2H, t, J = 2.0 Hz), 5.40 (s, 2H, isoxazole-CH₂), 6.70 (s, 1H, 1H of isoxazole), 7.47 (2H, d, J = 8.8 Hz), 7.79 (2H, d, J = 8.8 Hz), 11.0 (brs, 1H, —COOH).

YJP-54  4.47 (2 × 2H, t, J = 2.0 Hz), 4.88 (2 × 2H, t, J = 2.0 Hz), 5.43 (s, 2H, isoxazole-CH₂), 6.90 (s, 1H, 1H of isoxazole), 7.35-7.44 (m, 2H), 7.52 (dd, 1H, J = 1.2, 1.2 Hz), 7.77 (dd, 1H, J = 2.0 , 2.0 Hz), 11.0 (brs, 1H, —COOH).

YJP-55  4.47 (2 × 2H, t, J = 2.0 Hz), 4.88 (2 × 2H, t, J = 2.0 Hz), 5.42 (s, 2H, isoxazole-CH₂), 6.89 (s, 1H, 1H of isoxazole), 7.37 (dd, 1H, J = 2.0, 2.0 Hz), 7.54 (1H, d, J = 2.0 Hz), 7.73 (1H, d, J = 8.4 Hz), 11.0 (brs, 1H, —COOH).

TABLE 1-continued

¹H NMR data of the preferred compounds

Number ¹H NMR (400 MHz, CDCl₃)

YJP-56 4.47 (2 × 2H, t, J = 2.0 Hz), 4.88 (2 × 2H, t, J = 2.0 Hz), 5.40 (s, 2H, isoxazole-CH₂), 6.70 (s, 1H, 1H of isoxazole), 7.63 (2H, d, J = 8.8 Hz), 7.79 (2H, d, J = 8.4 Hz), 11.0 (brs, 1H, —COOH).

YJP-57 4.47 (2 × 2H, t, J = 2.0 Hz), 4.88 (2 × 2H, t, J = 2.0 Hz), 5.42 (s, 2H, isoxazole-CH₂), 6.87 (s, 1H, 1H of isoxazole), 7.18-7.26 (m, 2H), 7.43-7.49 (m, 1H), 7.99-8.04 (m, 1H), 11.0 (brs, 1H, —COOH).

YJP-58 4.47 (2 × 2H, t, J = 2.0 Hz), 4.88 (2 × 2H, t, J = 2.0 Hz), 5.40 (s, 2H, isoxazole-CH₂), 6.71 (s, 1H, 1H of isoxazole), 7.00-7.04 (m, 1H), 7.38-7.41 (m, 3H), 11.0 (brs, 1H, —COOH).

YJP-59 4.48 (2 × 2H, t, J = 2.0 Hz), 4.88 (2 × 2H, t, J = 2.0 Hz), 5.43 (s, 2H, isoxazole-CH₂), 6.80 (s, 1H, 1H of isoxazole), 8.04 (2H, d, J = 8.8 Hz), 7.79 (2H, d, J = 8.4 Hz), 11.0 (brs, 1H, —COOH).

YJP-60 4.47 (2 × 2H, t, J = 2.0 Hz), 4.88 (2 × 2H, t, J = 2.0 Hz), 5.40 (s, 2H, isoxazole-CH₂), 6.70 (s, 1H, 1H of isoxazole), 7.63 (2H, d, J = 8.8 Hz), 7.79 (2H, d, J = 8.4 Hz), 11.0 (brs, 1H, —COOH).

YJP-61 4.47 (2 × 2H, t, J = 2.0 Hz), 4.88 (2 × 2H, t, J = 2.0 Hz), 5.40 (s, 2H, isoxazole-CH₂), 5.66 (1H, t, NH—CO—, J = 4.6 Hz), 6.69 (s, 1H, 1H of isoxazole), 7.20 (2H, d, J = 8.8 Hz), 7.85 (2H, d, J = 8.8 Hz), 11.0 (brs, 1H, —COOH).

YJP-62 2.42 (s, 3H, CH₃), 4.46 (2 × 2H, t, J = 2.0 Hz), 4.88 (2 × 2H, t, J = 2.0 Hz), 5.40 (s, 2H, isoxazole-CH₂), 5.66 (1H, t, NH—CO—, J = 4.6 Hz), 6.70 (s, 1H, 1H of isoxazole), 7.28 (2H, d, J = 4.8 Hz), 7.74 (2H, d, J = 8.0 Hz), 11.0 (brs, 1H, —COOH).

YJP-63 1.29 (3H, CH₃, t, J = 7.6 Hz), 2.72 (2H, CH₃CH₂, q, J = 7.6 Hz), 4.46 (2 × 2H, t, J = 2.0 Hz), 4.88 (2 × 2H, t, J = 2.0 Hz), 5.40 (s, 2H, isoxazole-CH₂), 5.66 (1H, t, NH—CO—, J = 4.6 Hz), 6.70 (s, 1H, 1H of isoxazole), 7.32 (2H, d, J = 8.0 Hz), 7.74 (2H, d, J = 8.4 Hz), 11.0 (brs, 1H, —COOH).

YJP-64 1.37 (s, 9H, 3 × CH₃), 4.46 (2 × 2H, t, J = 2.0 Hz), 4.88 (2 × 2H, t, J = 2.0 Hz), 5.40 (s, 2H, isoxazole-CH₂), 5.66 (1H, t, NH—CO—, J = 4.6 Hz), 6.71 (s, 1H, 1H of isoxazole), 7.51 (2H, d, J = 8.4 Hz), 7.78 (2H, d, J = 6.8 Hz), 11.0 (brs, 1H, —COOH).

YJP-65 2.17 (s, 6H, 2 × CH₃), 2.34 (s, 3H, CH₃), 4.47 (2 × 2H, t, J = 2.0 Hz), 4.89 (2 × 2H, t, J = 2.0 Hz), 5.43 (s, 2H, isoxazole-CH₂), 5.66 (1H, t, NH—CO—, J = 4.6 Hz), 6.71 (s, 1H, 1H of isoxazole), 6.96 (s, 2H), 11.0 (brs, 1H, —COOH).

YJP-66 3.88 (s, 3H, OCH₃), 4.47 (2 × 2H, t, J = 2.0 Hz), 4.88 (2 × 2H, t, J = 2.0 Hz), 5.39 (s, 2H, isoxazole-CH₂), 5.66 (1H, t, NH—CO—, J = 4.6 Hz), 6.67 (s, 1H, 1H of isoxazole), 7.00 (d, 2H, J = 5.2 Hz), 7.79 (d, 2H, J = 9.2 Hz), 11.0 (brs, 1H, —COOH).

YJP-67 3.92 (s, 3H, OCH₃), 4.46 (2 × 2H, t, J = 2.0 Hz), 4.88 (2 × 2H, t, J = 2.0 Hz), 5.41 (s, 2H, isoxazole-CH₂), 5.66 (1H, t, NH—CO—, J = 4.6 Hz), 6.92 (s, 1H, 1H of isoxazole), 7.01-7.08 (m, 2H), 7.42-7.46 (m, 1H), 7.91 (1H, dd, J = 1.6, 2.0 Hz), 11.0 (brs, 1H, —COOH).

YJP-68 3.89 (s, 3H, OCH₃), 4.47 (2 × 2H, t, J = 2.0 Hz), 4.88 (2 × 2H, t, J = 2.0 Hz), 5.40 (s, 2H, isoxazole-CH₂), 5.66 (1H, t, NH—CO—, J = 4.6 Hz), 6.71 (s, 1H, 1H of isoxazole), 7.00-7.04 (m, 1H), 7.38-7.41 (m, 3H), 11.0 (brs, 1H, —COOH).

YJP-69 4.47 (2 × 2H, t, J = 2.0 Hz), 4.88 (2 × 2H, t, J = 2.0 Hz), 5.42 (s, 2H, isoxazole-CH₂), 5.66 (1H, t, NH—CO—, J = 4.6 Hz), 6.71 (s, 1H, 1H of isoxazole), 7.76 (2H, d, J = 8.4 Hz), 7.98 (2H, d, J = 8.4 Hz), 11.0 (brs, 1H, —COOH).

YJP-70 4.46 (2 × 2H, t, J = 2.0 Hz), 4.88 (2 × 2H, t, J = 2.0 Hz), 5.41 (s, 2H, isoxazole-CH₂), 5.66 (1H, t, NH—CO—, J = 4.6 Hz), 6.92 (s, 1H, 1H of isoxazole), 7.01-7.08 (m, 2H), 7.42-7.46 (m, 1H), 7.91 (1H, dd, J = 1.6, 2.0 Hz), 11.0 (brs, 1H, —COOH).

YJP-71 4.47 (2 × 2H, t, J = 2.0 Hz), 4.88 (2 × 2H, t, J = 2.0 Hz), 5.40 (s, 2H, isoxazole-CH₂), 5.66 (1H, t, NH—CO—, J = 4.6 Hz), 6.69 (s, 1H, 1H of isoxazole), 7.20 (2H, d, J = 8.8 Hz), 7.85 (2H, d, J = 8.8 Hz), 11.0 (brs, 1H, —COOH).

YJP-72 4.47 (2 × 2H, t, J = 2.0 Hz), 4.88 (2 × 2H, t, J = 2.0 Hz), 5.42 (s, 2H, isoxazole-CH₂), 5.66 (1H, t, NH—CO—, J = 4.6 Hz), 6.87 (s, 1H, 1H of isoxazole), 7.18-7.26 (m, 2H), 7.43-7.49 (m, 1H), 7.99-8.04 (m, 1H), 11.0 (brs, 1H, —COOH).

YJP-73 4.47 (2 × 2H, t, J = 2.0 Hz), 4.88 (2 × 2H, t, J = 2.0 Hz), 5.40 (s, 2H, isoxazole-CH₂), 5.66 (1H, t, NH—CO—, J = 4.6 Hz), 6.70 (s, 1H, 1H of isoxazole), 7.47 (2H, d, J = 8.8 Hz), 7.79 (2H, d, J = 8.8 Hz), 11.0 (brs, 1H, —COOH).

YJP-74 4.47 (2 × 2H, t, J = 2.0 Hz), 4.88 (2 × 2H, t, J = 2.0 Hz), 5.43 (s, 1H, isoxazole-CH₂), 5.66 (1H, t, NH—CO—, J = 4.6 Hz), 6.90 (s, 1H, 1H of isoxazole), 7.35-7.44 (m, 2H), 7.52 (dd, 1H, J = 1.2, 1.2 Hz), 7.77 (dd, 1H, J = 2.0, 2.0 Hz), 11.0 (brs, 1H, —COOH).

YJP-75 4.47 (2 × 2H, t, J = 2.0 Hz), 4.88 (2 × 2H, t, J = 2.0 Hz), 5.42 (s, 2H, isoxazole-CH₂), 5.66 (1H, t, NH—CO—, J = 4.6 Hz), 6.89 (s, 1H, 1H of isoxazole), 7.37 (dd, 1H, J = 2.0, 2.0 Hz), 7.54 (1H, d, J = 2.0 Hz), 7.73 (1H, d, J = 8.4 Hz), 11.0 (brs, 1H, —COOH).

YJP-76 4.47 (2 × 2H, t, J = 2.0 Hz), 4.88 (2 × 2H, t, J = 2.0 Hz), 5.40 (s, 2H, isoxazole-CH₂), 5.66 (1H, t, NH—CO—, J = 4.6 Hz), 6.70 (s, 1H, 1H of isoxazole), 7.63 (2H, d, J = 8.8 Hz), 7.79 (2H, d, J = 8.4 Hz), 11.0 (brs, 1H, —COOH).

YJP-77 4.47 (2 × 2H, t, J = 2.0 Hz), 4.88 (2 × 2H, t, J = 2.0 Hz), 5.42 (s, 2H, isoxazole-CH₂), 5.66 (1H, t, NH—CO—, J = 4.6 Hz), 6.87 (s, 1H, 1H of isoxazole), 7.18-7.26 (m, 2H), 7.43-7.49 (m, 1H), 7.99-8.04 (m, 1H), 11.0 (brs, 1H, —COOH).

YJP-78 4.47 (2 × 2H, t, J = 2.0 Hz), 4.88 (2 × 2H, t, J = 2.0 Hz), 5.40 (s, 2H, isoxazole-CH₂), 5.66 (1H, t, NH—CO—, J = 4.6 Hz), 6.71 (s, 1H, 1H of isoxazole), 7.00-7.04 (m, 1H), 7.38-7.41 (m, 3H), 11.0 (brs, 1H, —COOH).

YJP-79 4.48 (2 × 2H, t, J = 2.0 Hz), 4.88 (2 × 2H, t, J = 2.0 Hz), 5.43 (s, 2H, isoxazole-CH₂), 5.66 (1H, t, NH—CO—, J = 4.6 Hz), 6.80 (s, 1H, 1H of isoxazole), 8.04 (2H, d, J = 8.8 Hz), 7.79 (2H, d, J = 8.4 Hz), 11.0 (brs, 1H, —COOH).

YJP-80 4.47 (2 × 2H, t, J = 2.0 Hz), 4.88 (2 × 2H, t, J = 2.0 Hz), 5.40 (s, 2H, isoxazole-CH₂), 6.70 (s, 1H, 1H of isoxazole), 7.63 (2H, d, J = 8.8 Hz), 7.79 (2H, d, J = 8.4 Hz), 11.0 (brs, 1H, —COOH).

Example 6 In Vitro Anticancer Activity Assay

Colorectal cancer cell line HCT-116, human lung cancer cell line A549 and breast cancer cell line MCF-7 were screened by MTT assay.

Specific experimental procedure is as follows:

(1) seeding colorectal cancer cell line HCT-116 which is in logarithmic growth phase in 96-well culture plates, when the cells grew to 90%, adding 1 μL of the test sample at a concentration of $1 \times 10^{-4}$M, using three replicate wells of the concentration, and designing positive control (Gefitinib) and 1 μL of negative control (DMSO+cell culture medium+ MTT), culturing the cells for 48 h at 37° C. in 5% $CO_2$; (2) then adding 20 μL of 5 mg/mL MTT solution into each well, after gently shaking for a few minutes incubating for 3 to 4 hours, removing the culture fluid; (3) adding 100 μL of DMSO into each well, shaking at low speeds on a shaker for 10 minutes, fully dissolving the crystals. Using a wavelength-tunable microplate reader absorbance value (A595) was measured at 595 nm. Inhibitory ratio was calculated with the following formula:

$$\text{Inhibitory ratio (\%)} = \frac{A_{595\,control\,group} - A_{595\,treated\,group}}{A_{595\,control\,group}} \times 100\%$$

wherein, $IC_{50}$ values were calculated using the GraphPad Prism 5 software.

Experimental procedure for inhibition of human lung cancer cell line A549 and breast cancer cell line MCF-7 are the same as the procedure of colorectal cancer cell line HCT-116.

The inhibitory activity results of the preferred ferrocene derivative against human lung cancer cell line A549 and breast cancer cell line MCF-7 are shown in Table 2.

TABLE 2

Testing results of inhibitory activity of some exemplified ferrocene derivatives in Table 1 against A549, HCT116 and MCF-7

| Compound | $IC_{50}$ (μM) | | |
|---|---|---|---|
| | A549 | HCT116 | MCF-7 |
| YJP-1 | 252.2 | $1.038 \times 10^{11}$ | 990 |
| YJP-2 | 198.1 | 220.1 | 135.8 |
| YJP-3 | $1.925 \times 10^{12}$ | $6.086 \times 10^{10}$ | 86.76 |
| YJP-4 | 220.3 | 2180 | 149.7 |
| YJP-5 | 188.6 | $2.952 \times 10^{10}$ | 142.0 |
| YJP-6 | $9.377 \times 10^{8}$ | $3.807 \times 10^{7}$ | 182.5 |
| YJP-7 | 868.4 | $1.318 \times 10^{15}$ | 157.3 |
| YJP-8 | 142.5 | 236.0 | 137.8 |
| YJP-9 | $4.795 \times 10^{-5}$ | 982062 | 132.8 |
| YJP-11 | 2863 | $1.060 \times 10^{8}$ | 138.0 |
| YJP-12 | 167.5 | 148.9 | 158.8 |
| YJP-13 | 690.3 | 486.2 | 169.1 |
| YJP-14 | 450.0 | 227.6 | 171.7 |
| YJP-15 | 222.4 | 233.5 | 189.8 |
| YJP-16 | 250.7 | 63.9 | 155.8 |
| YJP-19 | 530.5 | 157.0 | 178.0 |
| Gefitinib | 21.55 | 17.9 | 20.68 |

The foregoing description refers to the examples of this invention. However, the present invention is not limited to the above-described examples. Any change such as modification, equivalent replacement, improvement, and so on, which may be made to these examples within the spirit and principles of the present invention, is intended to be embraced within the scope of the invention.

The invention claimed is:

1. A ferrocene derivative of formula (IA) or formula (IB), and a pharmaceutically acceptable salt or solvate thereof:

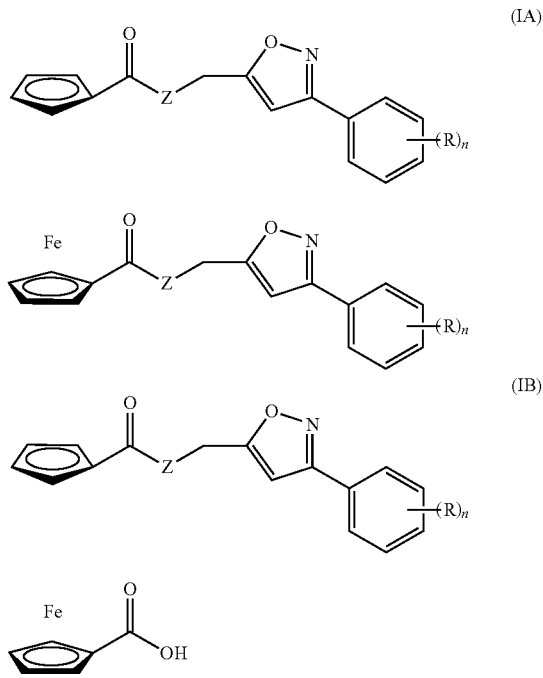

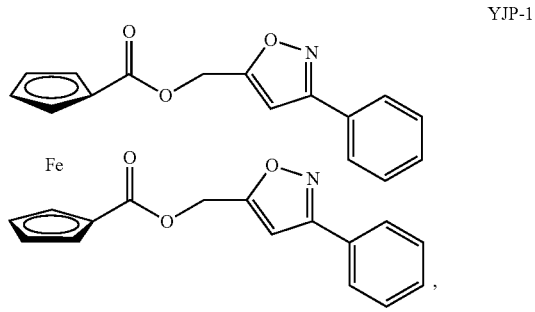

wherein:
Z is O, S or $NR_1$, wherein $R_1$ is independently H or $C_1$-$C_6$ alkyl;
R is independently selected from the group consisting of H, halogen, cyano, nitro, $C_1$-$C_6$ alkyl, $C_1$-$C_6$ alkoxy, hydroxy-$C_1$-$C_6$ alkyl, halo-$C_1$-$C_6$ alkyl, halo-$C_1$-$C_6$ alkoxy, and $C_1$-$C_6$ alkoxy-$C_1$-$C_6$ alkoxy; and
n is an integer from 0 to 5, and where n is more than 1, the R groups are the same or different.

2. The ferrocene derivative and the pharmaceutically acceptable salt or solvate thereof according to claim 1, wherein:
Z is O or $NR_1$, wherein $R_1$ is independently H or $C_1$-$C_4$ alkyl;
R is independently selected from the group consisting of H, halogen, cyano, nitro, $C_1$-$C_4$ alkyl, $C_1$-$C_4$ alkoxy, hydroxy-$C_1$-$C_3$ alkyl, and halo-$C_1$-$C_4$ alkyl;
n is an integer from 0 to 5.

3. The ferrocene derivative and the pharmaceutically acceptable salt or solvate thereof according to claim 1, wherein said ferrocene derivative is -continued
YJP-2
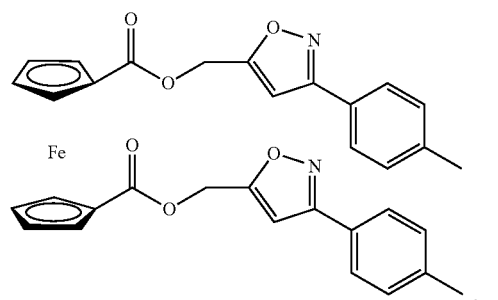
YJP-3
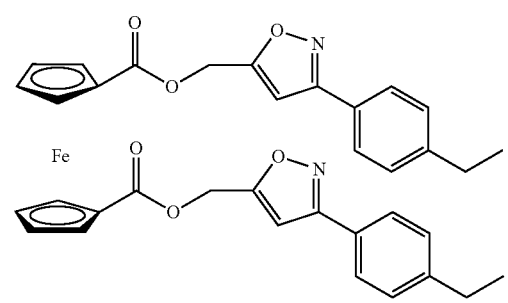
YJP-4
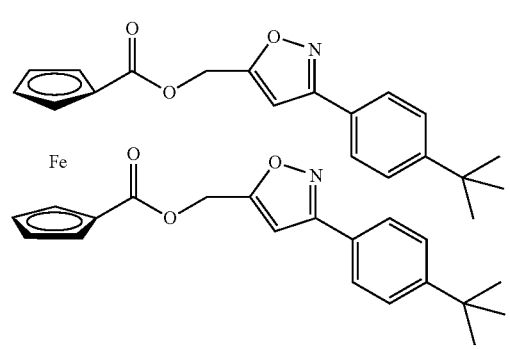
YJP-5
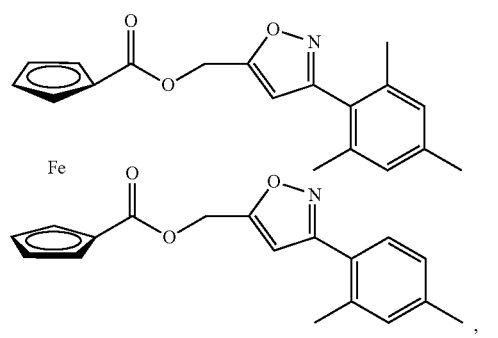
YJP-6
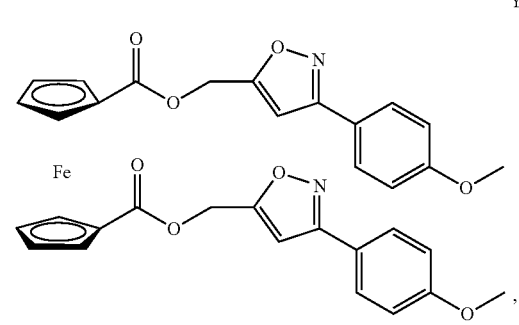
-continued
YJP-7
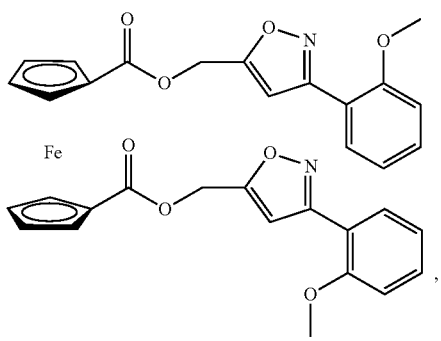
YJP-8
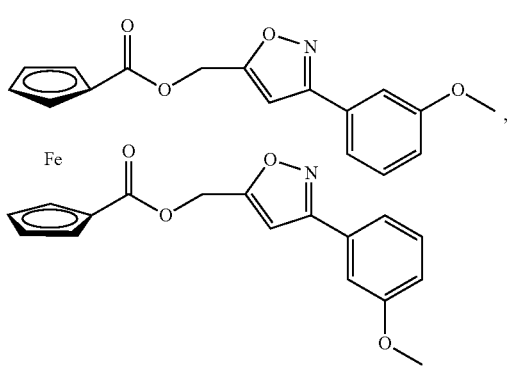
YJP-9
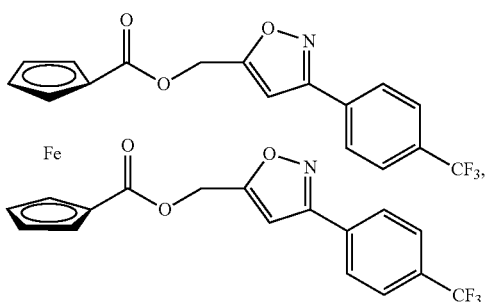
YJP-10
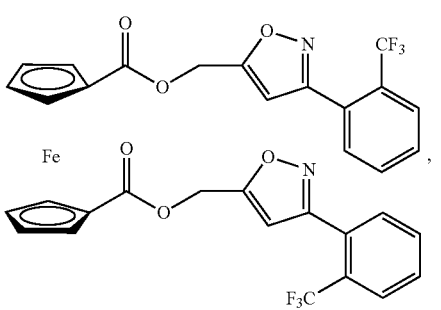
YJP-11
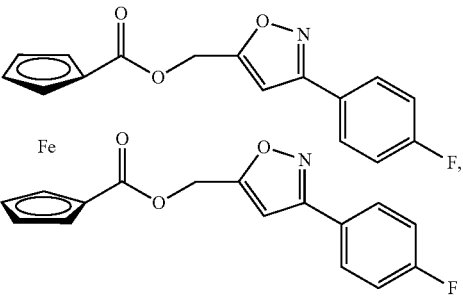

YJP-12
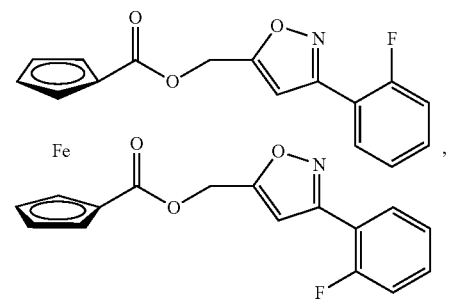
YJP-13
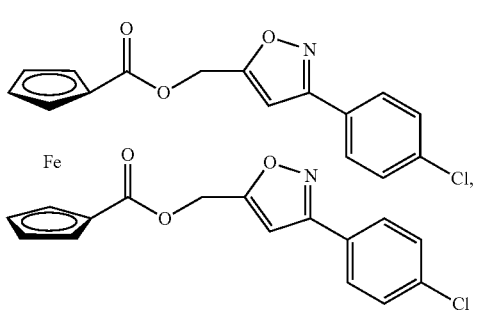
YJP-14
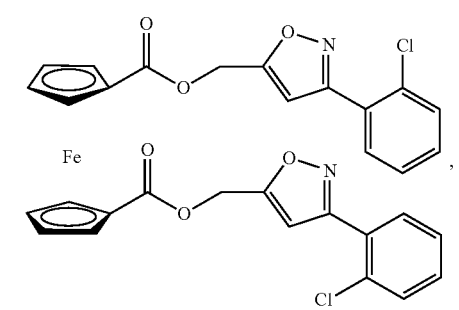
YJP-15
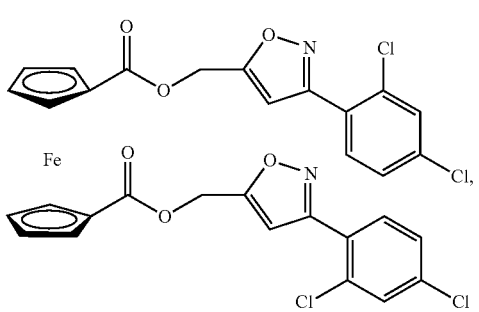
YJP-16
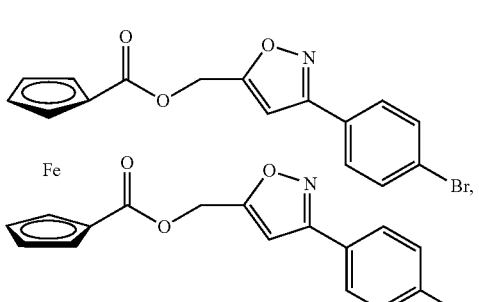
YJP-17
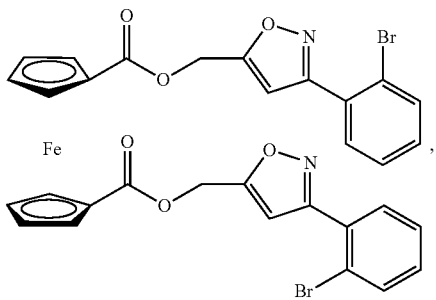
YJP-18
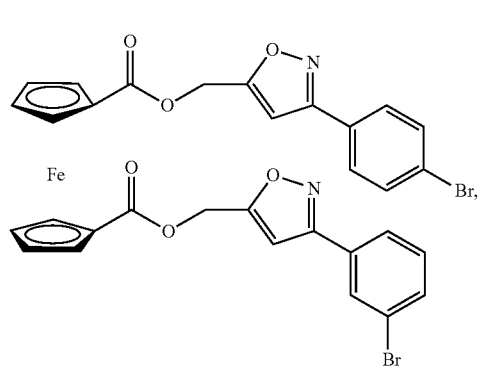
YJP-19
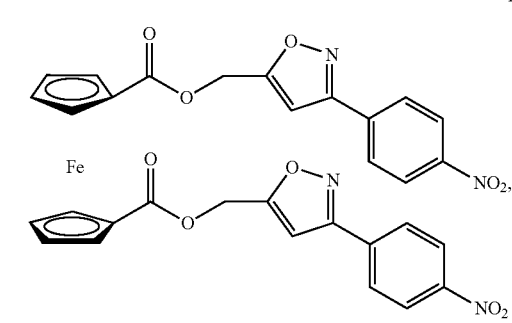
YJP-20
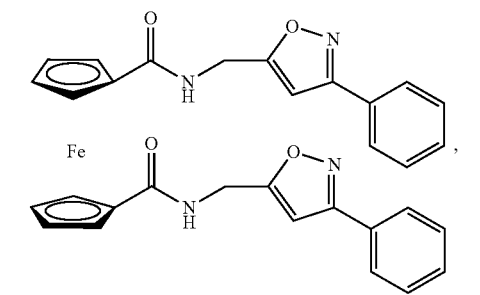
YJP-21
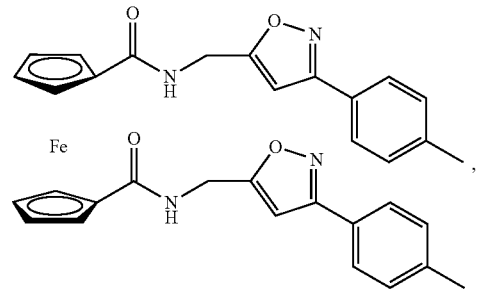

YJP-22
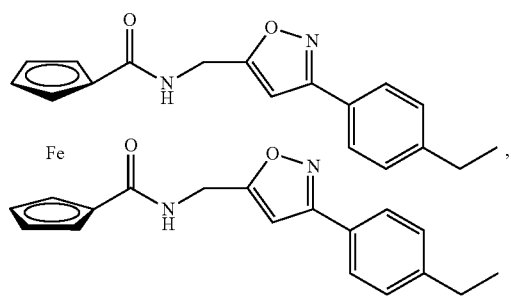
YJP-23
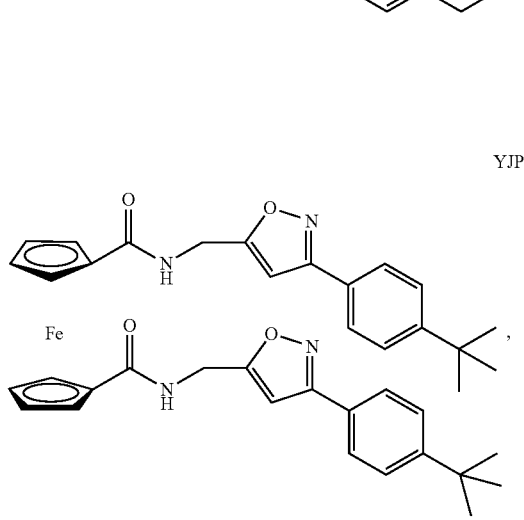
YJP-24
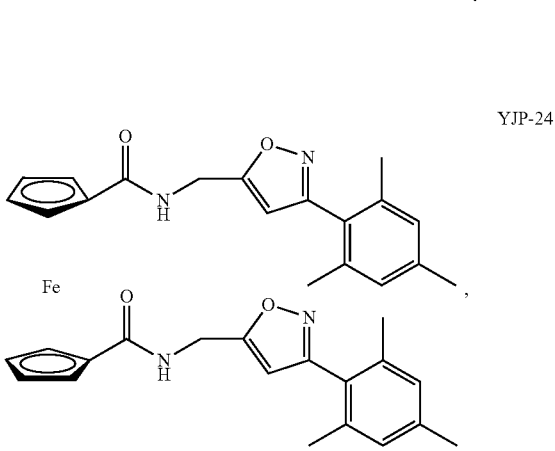
YJP-25
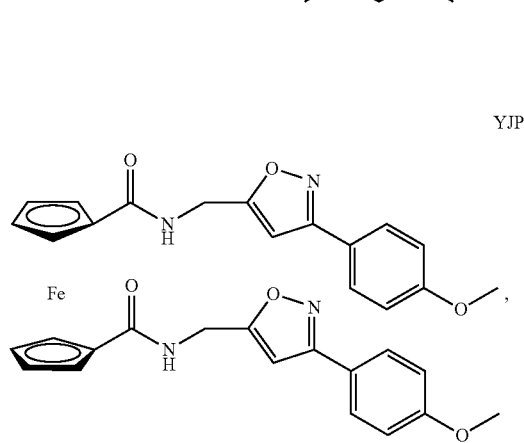
YJP-26
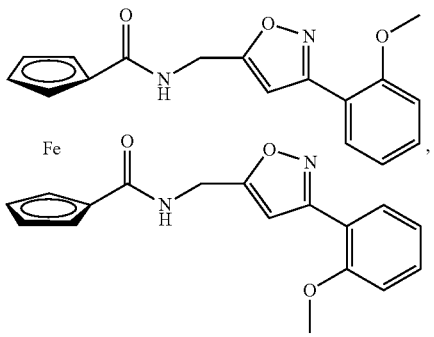
YJP-27
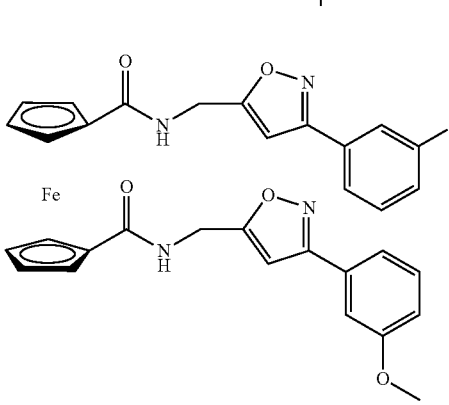
YJP-28
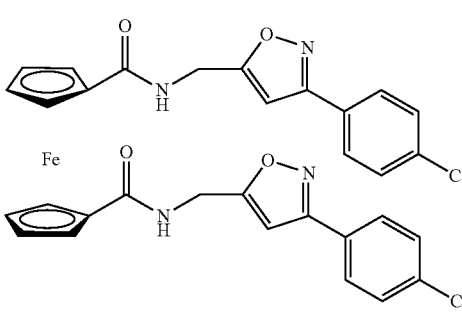
YJP-29
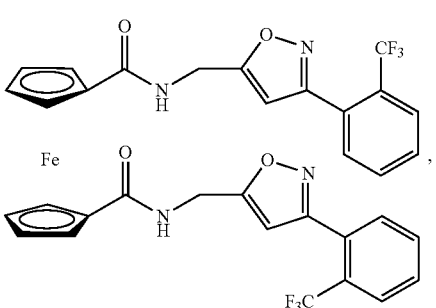
YJP-30
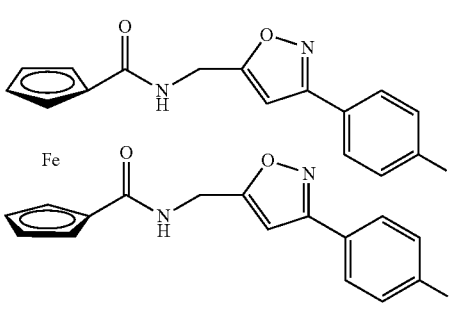

-continued
YJP-31
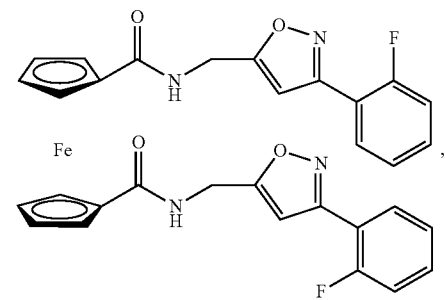
YJP-32
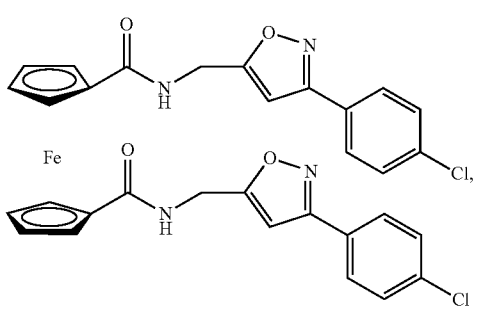
YJP-33
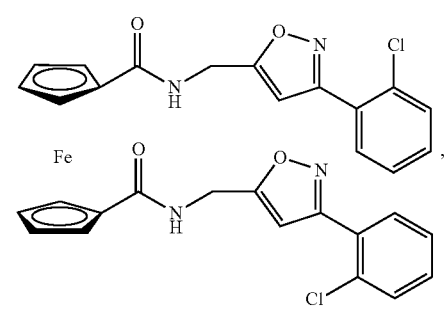
YJP-34
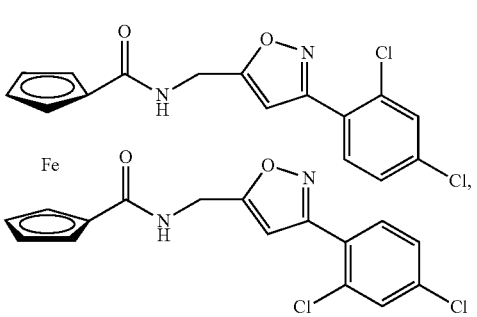
YJP-35
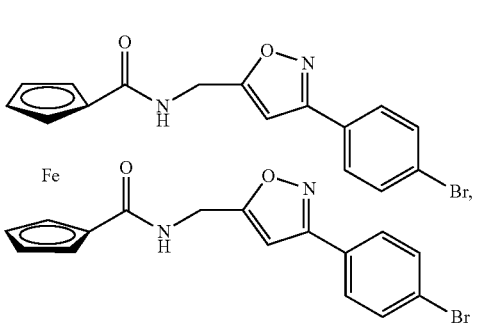
YJP-36
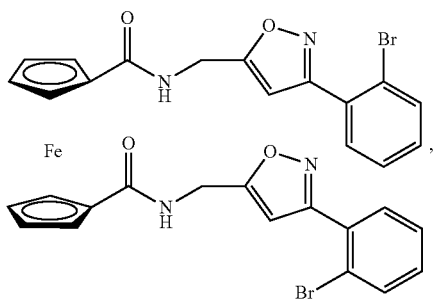
YJP-37
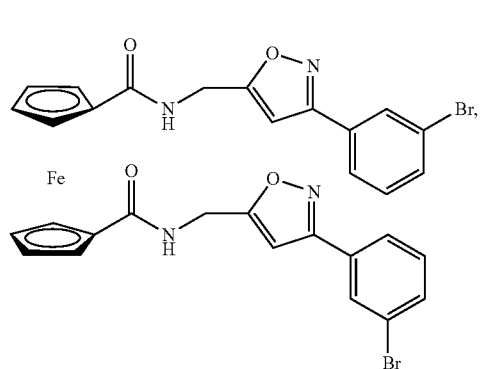
YJP-38
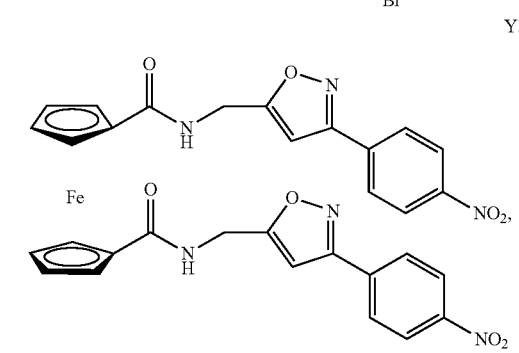
YJP-39
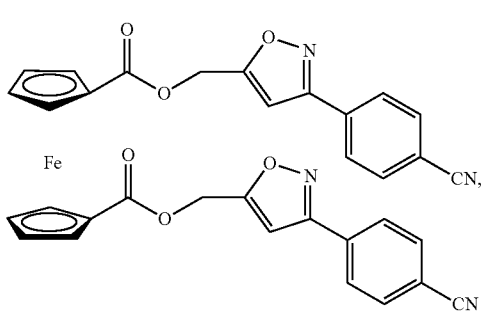
YJP-40
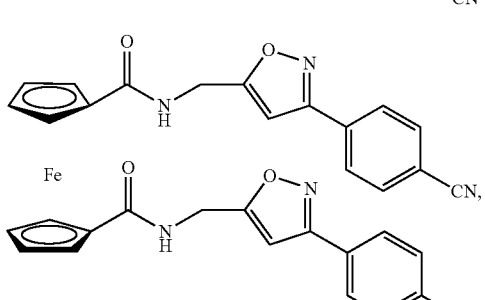

-continued
YJP-41
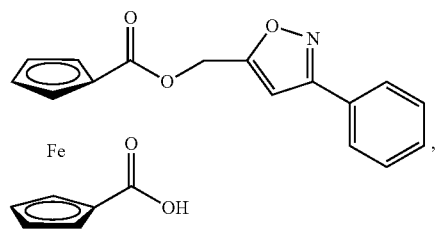
YJP-42
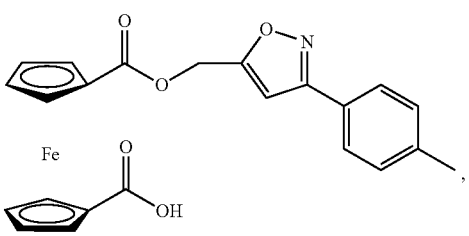
YJP-43
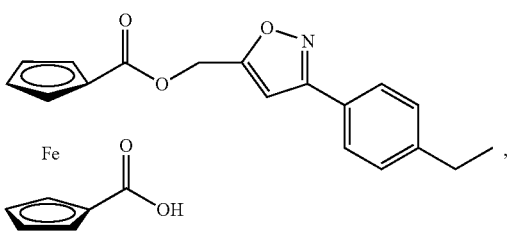
YJP-44
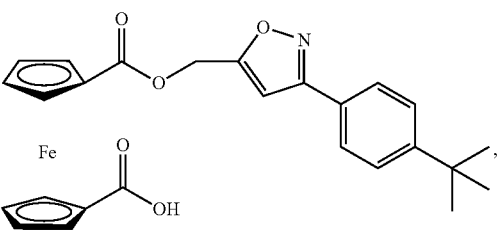
YJP-45
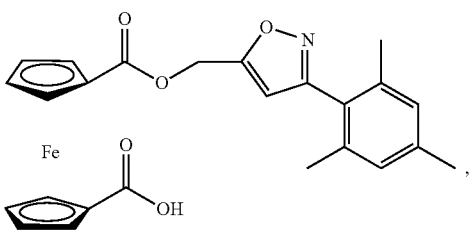
YJP-46
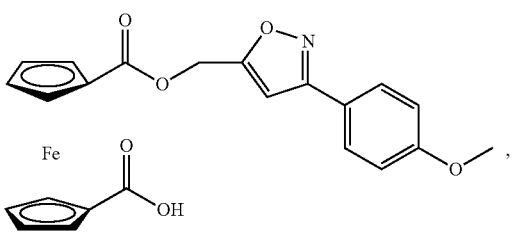
YJP-47
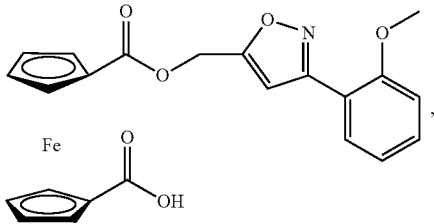
YJP-48
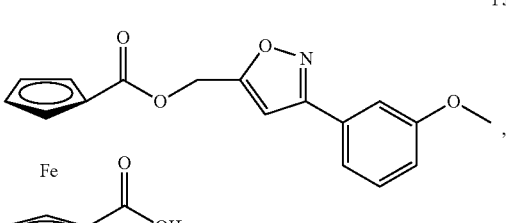
YJP-49
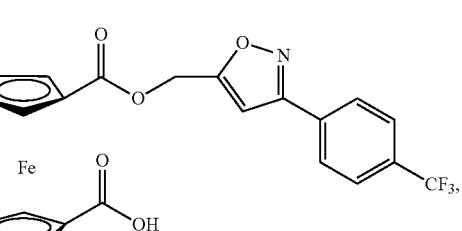
YJP-50
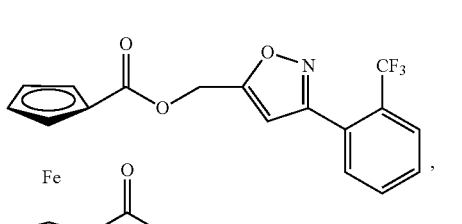
YJP-51
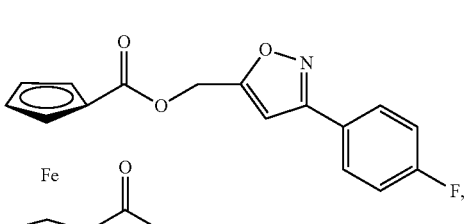
YJP-52
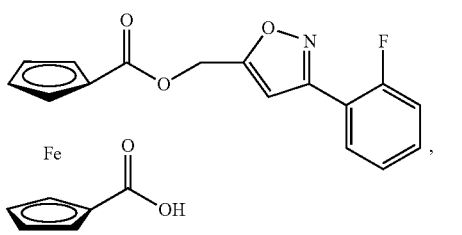

YJP-53

YJP-54

YJP-55

YJP-56

YJP-57

YJP-58

YJP-59

YJP-60

YJP-61

YJP-62

YJP-63

YJP-64

YJP-65

YJP-66

YJP-67

YJP-68

YJP-69

YJP-70

YJP-71

YJP-72

YJP-73

YJP-74

YJP-75

YJP-76

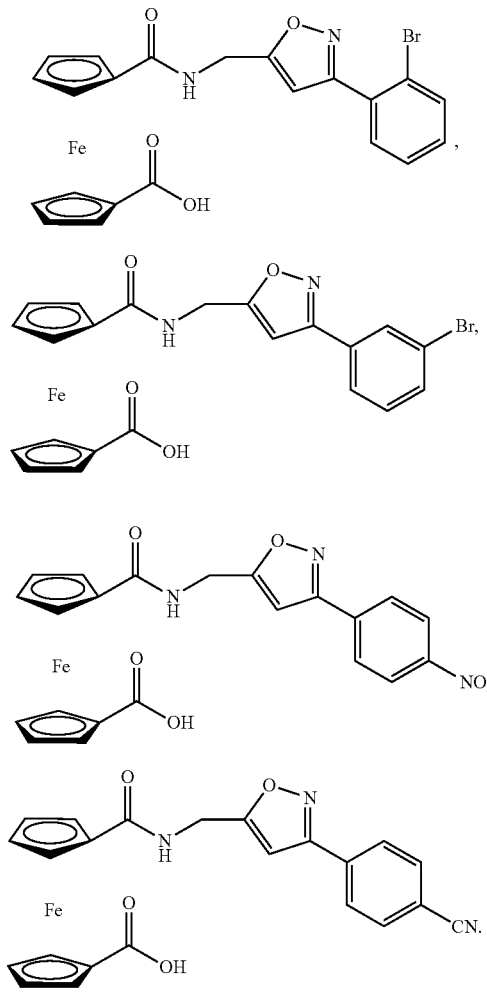

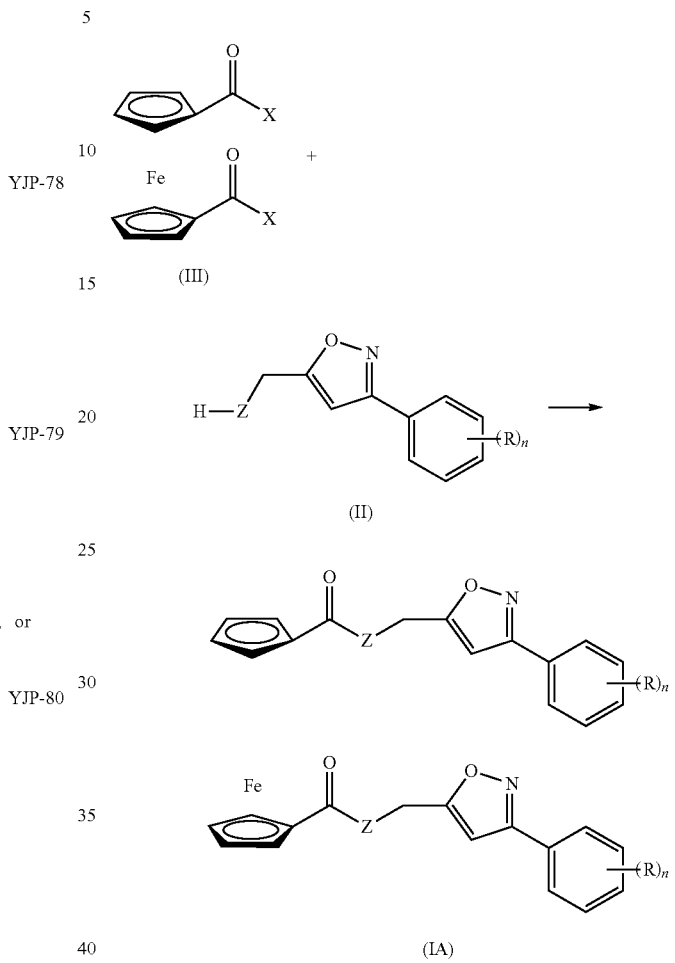

4. The ferrocene derivative and the pharmaceutically acceptable salt or solvate thereof according to claim 1, wherein the pharmaceutically acceptable salt comprises a salt formed with an inorganic acid.

5. A pharmaceutical composition, comprising: the ferrocene derivative according to claim 1, or the pharmaceutically acceptable salt or solvate thereof according to claim 1, or both, and at least one pharmaceutically acceptable excipient, carrier or diluent.

6. The pharmaceutical composition according to claim 5, wherein said pharmaceutical composition is in the form of a solid oral preparation, a liquid oral preparation or an injection.

7. A method of treating a tumor or a cancer, comprising: preparing a medicament comprising the ferrocene derivative according to claim 1, or the pharmaceutically acceptable salt or solvate thereof according to claim 1, or both; and administering the medicament to a patient in need thereof, wherein said tumor or cancer is associated with overexpression and/or overactivity of EGFR.

8. The method according to claim 7, wherein the medicament inhibits the overexpression and/or overactivity of EGFR.

9. A method for preparing said ferrocene derivative according to claim 1, comprising:
A) carrying out a condensation reaction between a compound of formula (III) and a compound of formula (II) in a system of an organic solvent and an alkaline acid binding reagent to obtain the compound of formula (IA):

wherein, X is optionally OH or Cl;

or,

B) carrying out a condensation reaction between 1,1'-ferrocenedicarboxylic acid and a compound of formula (II) in a system of an organic solvent and an alkaline catalyst to obtain the compound of formula (IB):

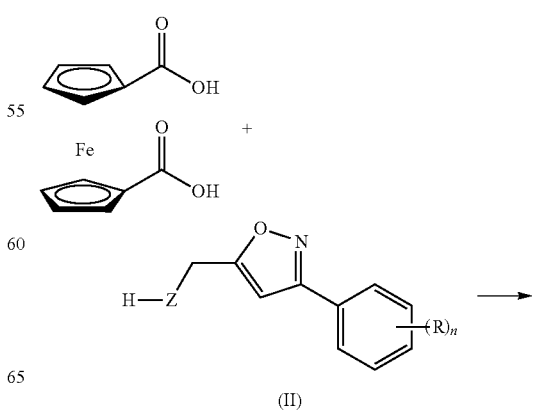

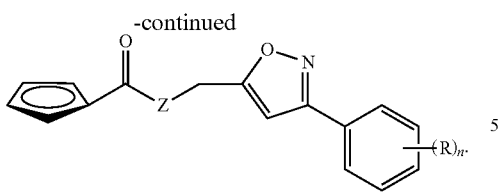

(IB)

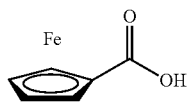

10. The pharmaceutical composition according to claim 5, wherein the pharmaceutically acceptable excipient, carrier, or diluent is selected from the group consisting of a filler, a disintegrating agent, a lubricant, a glidant, an effervescent agent, a flavoring agent, a preservative, and a coating material.

11. The pharmaceutical composition according to claim 6, wherein said preparation is a tablet, a dispersible tablet, an enteric coated tablet, a chewable tablet, an orally disintegrating tablet, a capsule, a granule, an oral soluble formulation, water for injection, a lyophilized powder for injection, a large volume infusion, or a small volume infusion.

12. The method according to claim 7, wherein said tumor or cancer is bladder cancer, non-small cell lung cancer, ovarian cancer, breast cancer, stomach cancer, esophageal cancer, lung cancer, head and neck cancer, colon cancer, pharyngeal cancer, pancreatic cancer, or non-small cell lung cancer.

13. The ferrocene derivative and the pharmaceutically acceptable salt or solvate thereof according to claim 4, wherein the inorganic acid is hydrochloride, phosphate, diphosphate, hydrobromide, sulfate, sulfinate, nitrate, and similar salts thereof; and also includes a salt formed with an organic acid, such as lactate, oxalate, malate, maleate, fumarate, tartrate, succinate, citrate, sulfonate, p-toluene sulfonate, 2-hydroxyethyl sulfonate, benzoate, salicylate, trifluoroacetate, amino acid salt, or alkanoate (such as acetate, stearate), or HOOC—$(CH_2)_m$—COOH salt, wherein m is an integer from 1 to 4.

14. The ferrocene derivative and the pharmaceutically acceptable salt or solvate thereof according to claim 1, wherein:
Z is O or NH;
R is independently selected from the group consisting of hydrogen, fluoro, chloro, bromo, methyl, ethyl, t-butyl, methoxy, nitro, cyano, and trifluoromethyl; and
n is 0, 1, 2, or 3.

15. The method for preparing said ferrocene derivative according to claim 9, further comprising:
protecting a functional group in formula (II) with a protecting reagent; and
removing the protective reagent from the compound of formula (IA) or formula (IB).

16. The method for preparing said ferrocene derivative according to claim 9, further comprising: forming a pharmaceutically acceptable salt of the compound of formula (IA) or formula (IB).

17. The method for preparing said ferrocene derivative according to claim 9, wherein the compound of formula (II) is a compound of formula (II-A), a compound of formula (II-B), or a compound of formula (II-C), wherein formula (II-A) is prepared by a method comprising: when Z is O, converting a compound of formula (1) to a compound of formula (2), and converting a compound of formula (2) to the compound of formula (II-A) via 1,3-dipolar cycloaddition reaction:

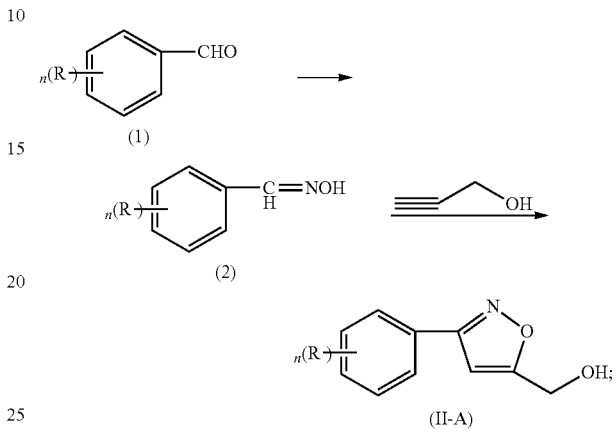

wherein formula (II-C) is prepared by a method comprising: when Z is S, converting a compound of formula (1) to a compound of formula (2), and converting a compound of formula (2) to the compound of formula (II-C) via 1,3-dipolar cycloaddition reaction:

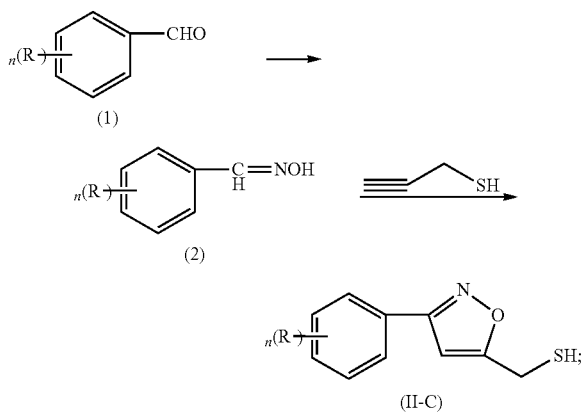

wherein formula (II-B) is prepared by a method comprising:

when Z is NH, 1) converting a compound of formula (II-A) via methylsulfonyl-esterification reaction, azidation and reduction to the compound of formula (II-A) to the compound of formula (II-B):

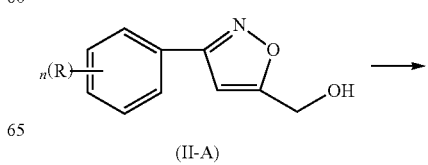

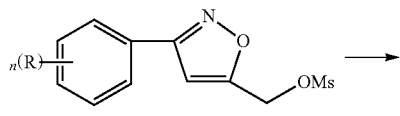
(3)
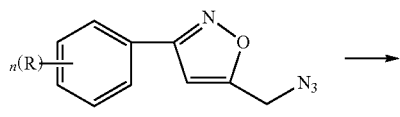
(4)
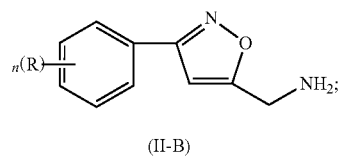
(II-B)
or, 2) reacting a compound of formula (2) and propargylamine via 1,3-dipolar cycloaddition reaction to obtain the compound of formula (II-B):
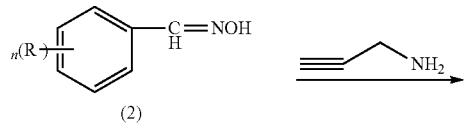
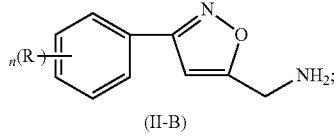
(II-B)
or, 3) reacting a compound of formula (2) and 3-halopropynyl via 1,3-dipolar cycloaddition reaction to obtain the compound of formula (5), followed by amine substitution reaction to obtain the compound of formula (II-B):
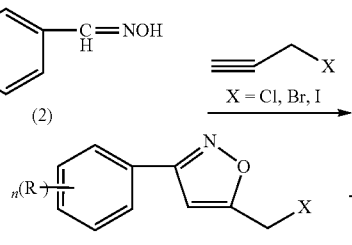
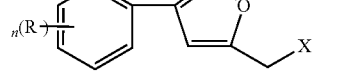
(5)
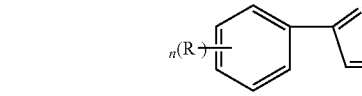
(II-B)
* * * * *